(12) United States Patent
Epstein

(10) Patent No.: US 7,025,755 B2
(45) Date of Patent: Apr. 11, 2006

(54) MEDICAL SUCTIONING APPARATUS AND METHODS OF USE

(75) Inventor: Gordan Howard Epstein, Fremont, CA (US)

(73) Assignee: Baxter International Inc., Deerfield, IL (US)

( * ) Notice: Subject to any disclaimer, the term of this patent is extended or adjusted under 35 U.S.C. 154(b) by 144 days.

(21) Appl. No.: 10/161,100

(22) Filed: May 31, 2002

(65) Prior Publication Data

US 2002/0173744 A1  Nov. 21, 2002

Related U.S. Application Data

(60) Continuation of application No. 09/426,353, filed on Oct. 25, 1999, now Pat. No. 6,471,667, which is a continuation of application No. 08/839,614, filed on Apr. 14, 1997, now Pat. No. 5,971,956, and a division of application No. 08/838,078, filed on Apr. 14, 1997, now Pat. No. 6,331,172.

(51) Int. Cl.
*A61M 31/00* (2006.01)

(52) U.S. Cl. .................. 604/500; 604/28; 604/119; 604/35; 604/30; 604/57; 604/45; 604/33; 137/625.4; 251/322

(58) Field of Classification Search .......... 604/27–35, 604/39, 43, 45, 57, 59, 61, 63, 118, 119, 500, 604/902, 47, 82, 73, 131, 135, 134, 173, 604/181, 187, 191, 218, 224; 606/94, 214, 606/213, 15; 239/113; 251/322; 137/625.4; 433/100; 222/387, 340, 137, 327, 391; 144/346, 144/329; 134/21

See application file for complete search history.

(56) References Cited

U.S. PATENT DOCUMENTS 1,206,126 A  11/1916  Mitsch (Continued)

FOREIGN PATENT DOCUMENTS

DE  G8133489.3  5/1982

(Continued)

OTHER PUBLICATIONS

PCT International Search Report, PCT/US98/07488, Jul. 8, 1998.

(Continued)

*Primary Examiner*—Loan H. Thanh
*Assistant Examiner*—Cris L. Rodriguez
(74) *Attorney, Agent, or Firm*—Jeffrey C. Nichols

(57) ABSTRACT

A medical fluid suctioning device for selectively applying varied levels of suction pressure at a device-tissue interface includes a direct "trumpet"-type control mechanism in conjunction with a "venturi"-type control. A valve manifold is adapted to couple a vent pathway and a suction pathway simultaneously to the vacuum conduit adapted for connection to a vacuum source. The amount of resistance to flow due to vacuum pressure is adjusted simultaneously in both the vent pathway and the suction pathway in order to achieve controlled, selected levels of suction. Similarly shaped valve apertures are provided in inverse and reciprocal orientation along an axis of motion of a valve manifold. The apertures translate across ports to the suction and venting pathways simultaneously to vary applied suction to those pathways inversely. The shaped valve apertures preferably have diminished elliptical shapes having an elongate axis with an increasing cross-sectional area going from a transverse short axis to a transverse wide axis along the axis of motion of the valve manifold. The diminished elliptical shapes are inversely oriented relative to each other as regards the positioning of their wide and short transverse axis along the axis of motion.

16 Claims, 15 Drawing Sheets

U.S. PATENT DOCUMENTS

| | | | |
|---|---|---|---|
| 1,889,425 | A | 11/1932 | Sorensen |
| 2,158,593 | A | 5/1939 | Scrimgeour |
| 2,576,766 | A | 11/1951 | Sokolik |
| 2,812,765 | A | 11/1957 | Tofflemire |
| 3,065,749 | A | 11/1962 | Brass |
| 3,071,402 | A | 1/1963 | Lasto |
| 3,159,312 | A | 12/1964 | Van Sciver, II |
| 3,179,107 | A | 4/1965 | Clark |
| 3,188,056 | A | 6/1965 | Trumbull |
| 3,208,145 | A | 9/1965 | Turner |
| 3,469,582 | A | 9/1969 | Jackson |
| 3,625,221 | A | 12/1971 | Corbett |
| 3,626,928 | A | 12/1971 | Barringer |
| 3,645,497 | A | 2/1972 | Nyboer |
| 3,767,085 | A | 10/1973 | Cannon |
| 3,794,039 | A * | 2/1974 | Kollner et al. ............... 606/22 |
| 3,812,855 | A * | 5/1974 | Banko ......................... 604/31 |
| 3,814,249 | A * | 6/1974 | Eaton .......................... 210/86 |
| 3,828,980 | A | 8/1974 | Creighton |
| 3,938,550 | A * | 2/1976 | Hechler, IV ................ 137/559 |
| 3,949,748 | A | 4/1976 | Malmin |
| 4,040,420 | A | 8/1977 | Speer |
| 4,043,042 | A | 8/1977 | Perfect |
| 4,067,479 | A | 1/1978 | Moline |
| 4,109,653 | A | 8/1978 | Kozam |
| 4,193,406 | A | 3/1980 | Jinotti |
| 4,223,676 | A | 9/1980 | Wuchinich |
| 4,266,545 | A | 5/1981 | Moss |
| 4,270,525 | A | 6/1981 | Furihata |
| 4,294,251 | A | 10/1981 | Greenwald |
| 4,299,221 | A * | 11/1981 | Phillips et al. ............. 128/276 |
| 4,325,913 | A | 4/1982 | Wardlaw |
| 4,356,823 | A | 11/1982 | Jackson |
| 4,359,049 | A | 11/1982 | Redl et al. |
| 4,397,640 | A | 8/1983 | Haug et al. |
| 4,445,517 | A | 5/1984 | Feild |
| 4,487,600 | A | 12/1984 | Brownlie et al. |
| 4,504,266 | A | 3/1985 | Harle |
| 4,519,385 | A | 5/1985 | Atkinson |
| 4,573,979 | A | 3/1986 | Blake |
| 4,617,013 | A | 10/1986 | Betz |
| 4,629,455 | A | 12/1986 | Kanno |
| 4,631,055 | A | 12/1986 | Redl et al. |
| 4,680,026 | A * | 7/1987 | Weightman et al. .......... 604/33 |
| 4,696,669 | A | 9/1987 | Menhusen |
| 4,699,138 | A | 10/1987 | Behrstock |
| 4,708,717 | A | 11/1987 | Deane et al. |
| 4,735,616 | A | 4/1988 | Eibl et al. |
| 4,743,229 | A | 5/1988 | Chu |
| 4,759,349 | A | 7/1988 | Betz |
| 4,776,840 | A | 10/1988 | Freitas et al. |
| 4,813,871 | A * | 3/1989 | Friedman ..................... 433/90 |
| 4,813,926 | A * | 3/1989 | Kerwin ....................... 604/118 |
| 4,842,581 | A | 6/1989 | Davis |
| 4,857,047 | A | 8/1989 | Amoils |
| 4,869,400 | A * | 9/1989 | Jacobs ........................ 222/137 |
| 4,874,368 | A | 10/1989 | Miller et al. |
| 4,891,044 | A | 1/1990 | Mitchell |
| 4,904,238 | A | 2/1990 | Williams |
| 4,925,447 | A | 5/1990 | Rosenblatt |
| 4,935,006 | A | 6/1990 | Hasson |
| 4,941,872 | A | 7/1990 | Felix |
| 4,967,933 | A * | 11/1990 | Maiorca et al. ................ 222/1 |
| 4,969,669 | A | 11/1990 | Sauer |
| 4,978,336 | A | 12/1990 | Capozzi et al. |
| 4,979,942 | A | 12/1990 | Wolf et al. |
| 4,981,473 | A | 1/1991 | Rosenblatt |
| 5,024,615 | A | 6/1991 | Buchel |
| 5,024,654 | A | 6/1991 | Tyler |
| 5,029,580 | A * | 7/1991 | Radford et al. ......... 128/207.14 |
| 5,045,055 | A | 9/1991 | Gonser |
| 5,049,135 | A | 9/1991 | Davis |
| 5,061,180 | A | 10/1991 | Wiele |
| 5,066,276 | A * | 11/1991 | Wang ......................... 604/51 |
| 5,105,985 | A * | 4/1992 | Kroeber ....................... 222/107 |
| 5,116,315 | A | 5/1992 | Capozzi et al. |
| 5,120,305 | A | 6/1992 | Boehringer |
| 5,145,367 | A | 9/1992 | Kasten |
| 5,163,433 | A * | 11/1992 | Kagawa et al. ......... 128/660.01 |
| 5,186,714 | A | 2/1993 | Boudreault et al. |
| 5,217,465 | A | 6/1993 | Steppe |
| 5,226,877 | A * | 7/1993 | Epstein ........................ 604/35 |
| 5,246,455 | A | 9/1993 | Shikani |
| 5,295,956 | A | 3/1994 | Bales et al. |
| 5,300,022 | A | 4/1994 | Klapper et al. |
| 5,304,165 | A | 4/1994 | Haber |
| 5,314,412 | A | 5/1994 | Rex |
| 5,318,782 | A | 6/1994 | Weis-Fogh |
| 5,328,459 | A * | 7/1994 | Laghi .......................... 604/35 |
| 5,348,542 | A | 9/1994 | Ellis |
| 5,368,560 | A | 11/1994 | Rambo et al. |
| 5,368,563 | A | 11/1994 | Lonneman et al. |
| 5,372,585 | A * | 12/1994 | Tiefenbrun et al. ............ 604/59 |
| 5,395,326 | A | 3/1995 | Haber et al. |
| 5,402,770 | A * | 4/1995 | Iida et al. .................... 600/159 |
| 5,405,607 | A | 4/1995 | Epstein |
| 5,419,769 | A | 5/1995 | Devlin et al. |
| 5,433,705 | A | 7/1995 | Giebel et al. |
| 5,447,494 | A | 9/1995 | Dorsey, III |
| 5,474,540 | A | 12/1995 | Miller et al. |
| 5,476,450 | A | 12/1995 | Ruggio |
| 5,480,487 | A * | 1/1996 | Figini et al. ................. 118/610 |
| 5,520,658 | A | 5/1996 | Holm |
| 5,520,685 | A | 5/1996 | Wojciechowicz |
| 5,536,254 | A * | 7/1996 | McVay ....................... 604/147 |
| 5,545,460 | A * | 8/1996 | Tanaka et al. ............... 428/137 |
| 5,551,603 | A * | 9/1996 | Woodruff ..................... 222/325 |
| 5,571,081 | A * | 11/1996 | Adhoute ........................ 604/4 |
| 5,582,596 | A * | 12/1996 | Fukunaga et al. .......... 604/191 |
| 5,584,815 | A | 12/1996 | Pawelka et al. |
| 5,585,007 | A | 12/1996 | Antanavich |
| 5,603,700 | A | 2/1997 | Daneshvar |
| 5,605,255 | A | 2/1997 | Reidel et al. |
| 5,605,541 | A | 2/1997 | Holm |
| 5,612,050 | A | 3/1997 | Rowe et al. |
| 5,648,265 | A | 7/1997 | Epstein |
| 5,692,642 | A * | 12/1997 | Brattesani ..................... 222/1 |
| 5,695,472 | A | 12/1997 | Wyrick |
| 5,749,968 | A * | 5/1998 | Melanson et al. .......... 118/300 |
| 5,759,171 | A | 6/1998 | Coelho et al. |
| 5,779,108 | A * | 7/1998 | Barriac et al. ............... 222/340 |
| 5,830,214 | A * | 11/1998 | Flom et al. .................... 606/41 |
| 5,902,264 | A | 5/1999 | Toso |
| 5,911,343 | A * | 6/1999 | Keller ....................... 222/145.1 |
| 5,975,367 | A | 11/1999 | Coelho |
| 5,989,215 | A | 11/1999 | Delmotte |
| 6,007,515 | A * | 12/1999 | Epstein et al. ................. 604/82 |
| 6,063,055 | A * | 5/2000 | Epstein et al. ................. 604/82 |

FOREIGN PATENT DOCUMENTS

| | | |
|---|---|---|
| DE | 3701190 | 7/1988 |
| DE | 4223356 | 1/1994 |
| EP | 0037393 | 4/1981 |
| EP | 302411 A2 | 2/1989 |
| EP | 0156098 | 11/1989 |
| EP | 0315222 | 11/1992 |
| EP | 592242 A1 | 4/1994 |
| EP | 0634140 | 1/1995 |
| WO | WO/95/31137 | 11/1995 |
| WO | WO 9619940 | 7/1996 |
| WO | WO/97/28834 | 8/1997 |

OTHER PUBLICATIONS

PCT International Search Report, PCT/US98/07846, Jul. 18, 1998.
Epstein, U.S. Appl. No. 08/646,464, These documents are not submitted herewith.
Epstein, U.S. Appl. No. 08/703,148, These documents are not submitted herewith.
Epstein, et al., U.S. Appl. No. 08/839,614, These documents are not submitted herewith.
Epstein, U.S. Appl. No. 08/863,883, These documents are not submitted herewith.
Epstein, et al., U.S. Appl. No. 08/946,364, These documents are not submitted herewith.
Schematic entitled "Common Caulking Gun" with description.

* cited by examiner

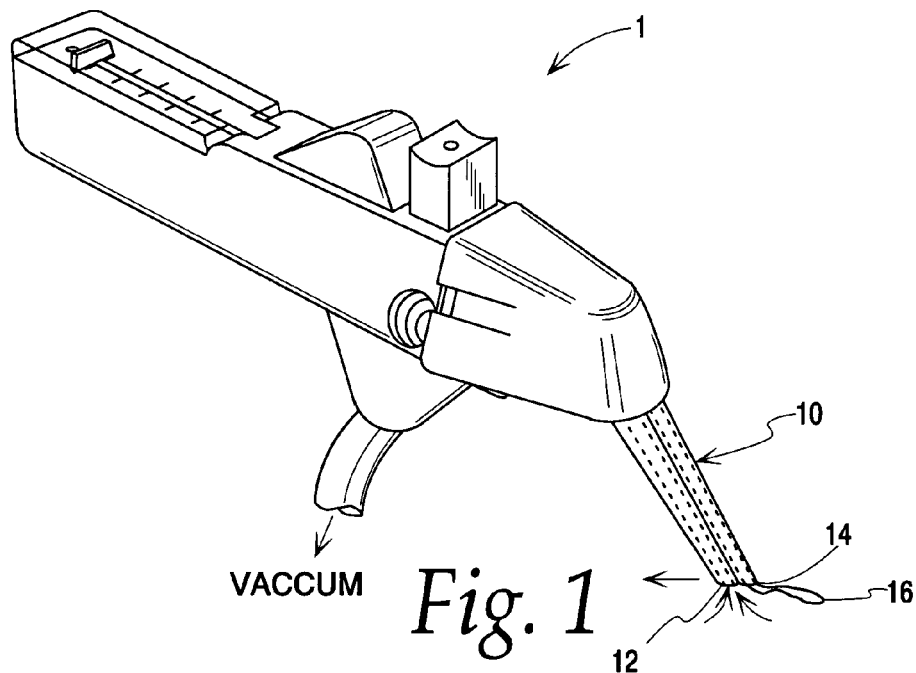
Fig. 1
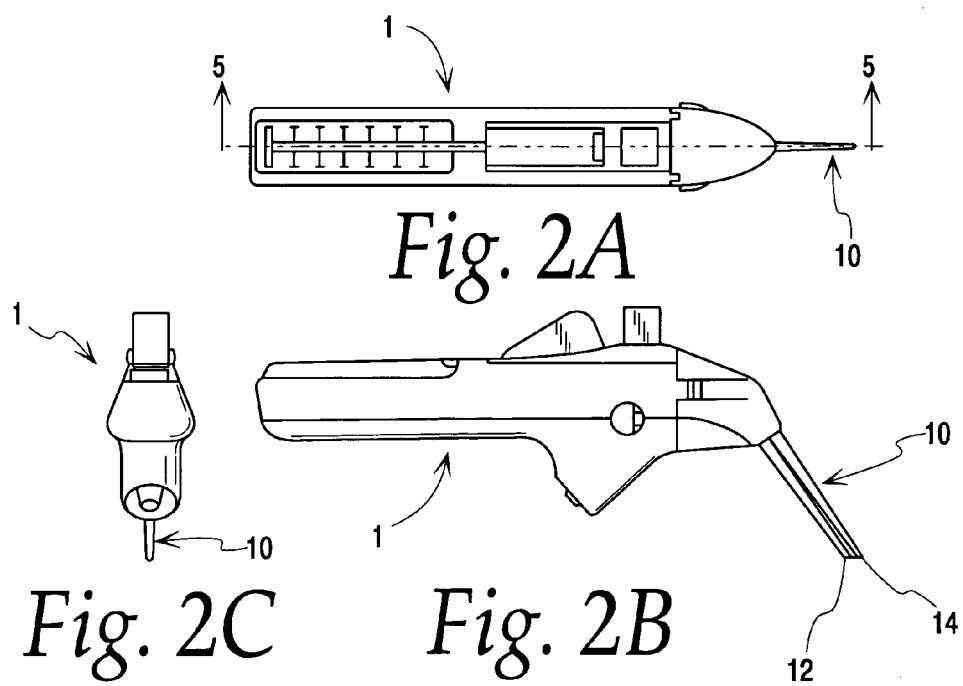
Fig. 2A
Fig. 2C  Fig. 2B

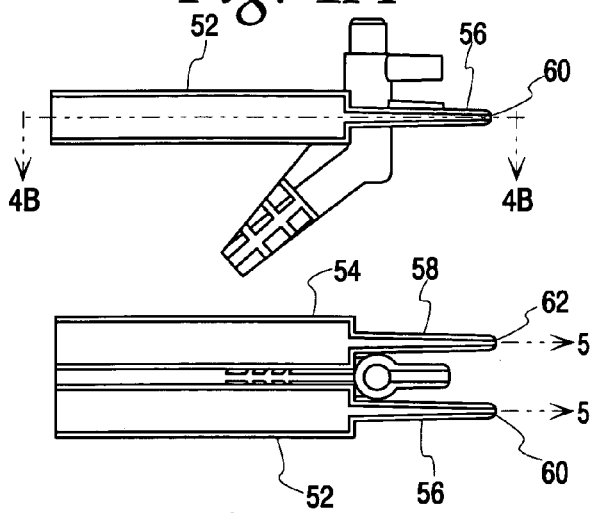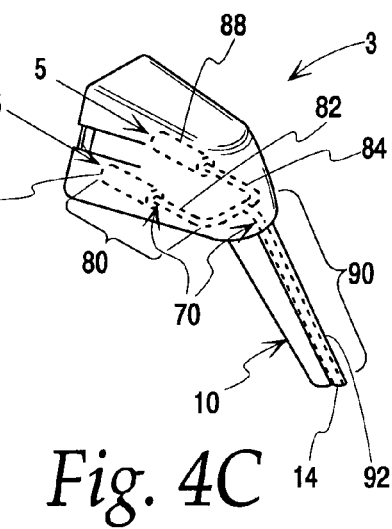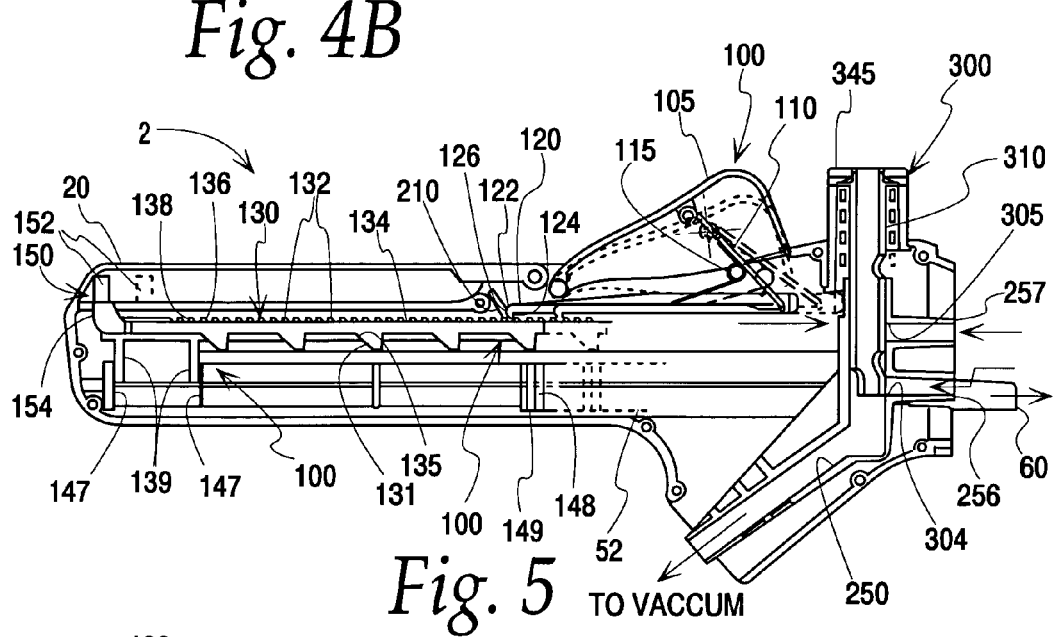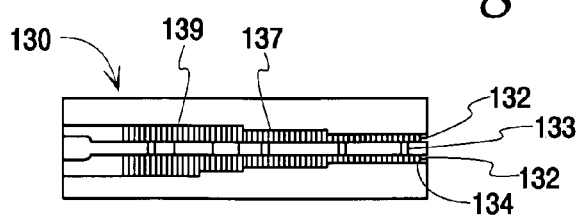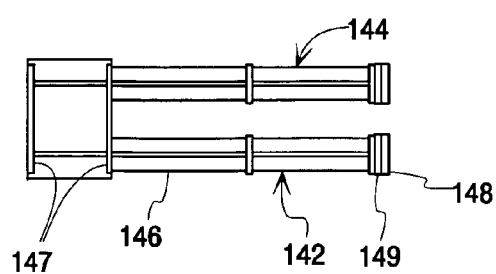

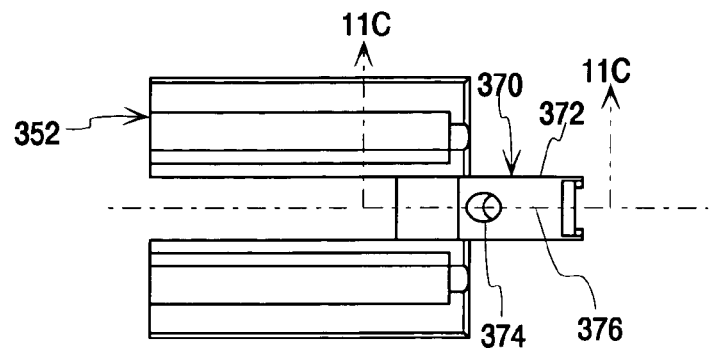
Fig. 11A
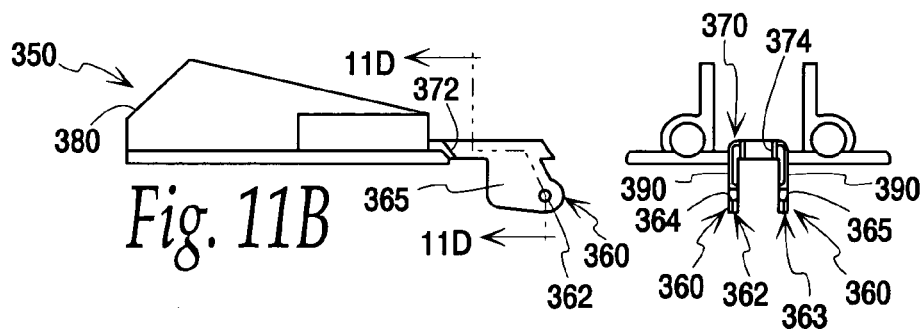
Fig. 11B
Fig. 11D
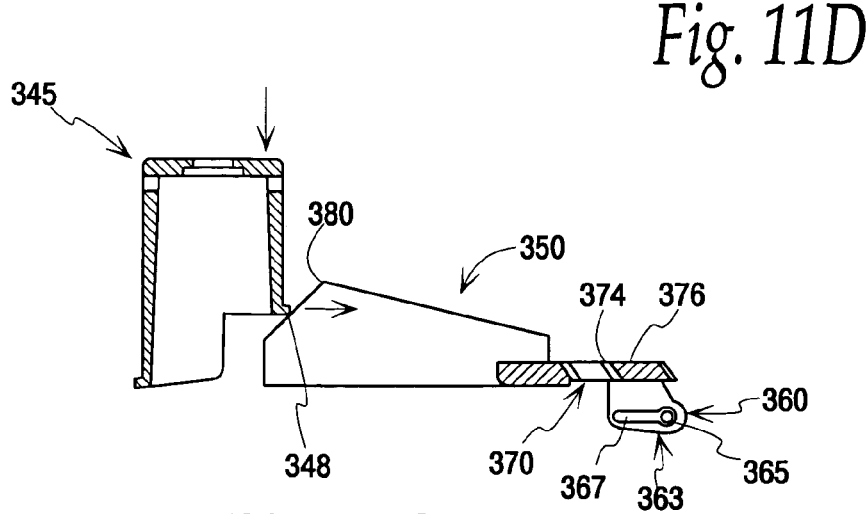
Fig. 11C

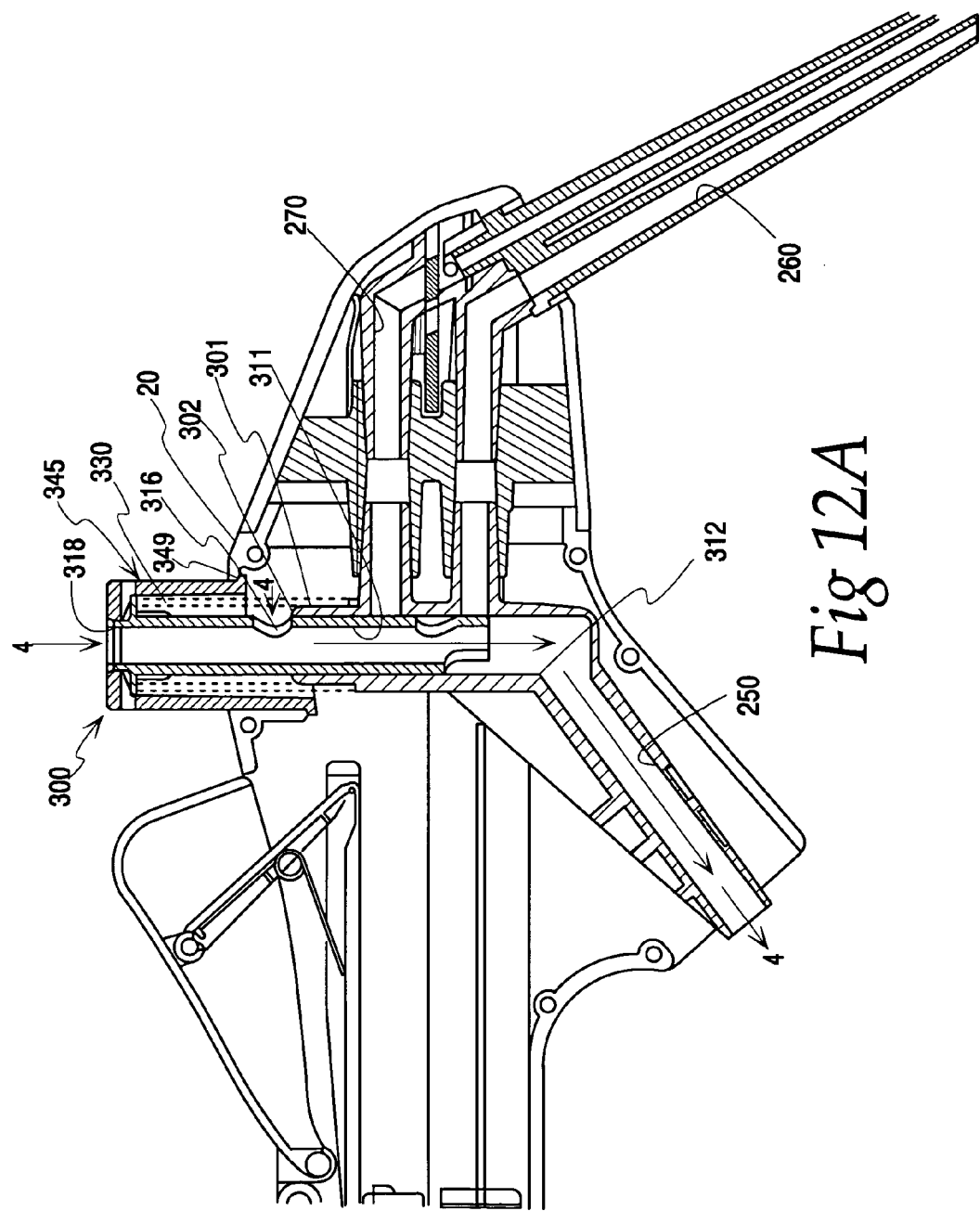

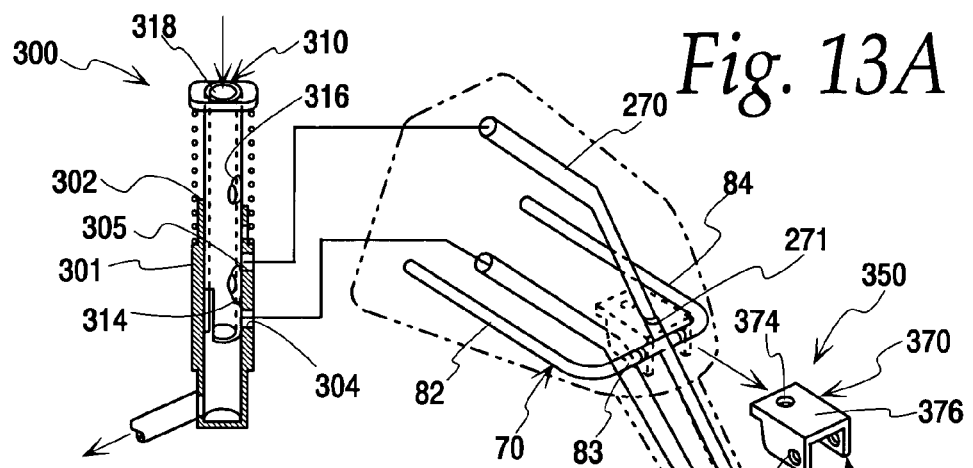
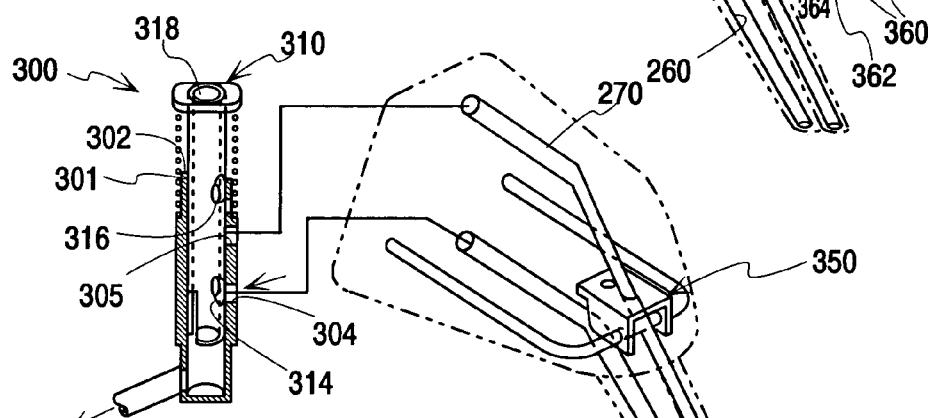
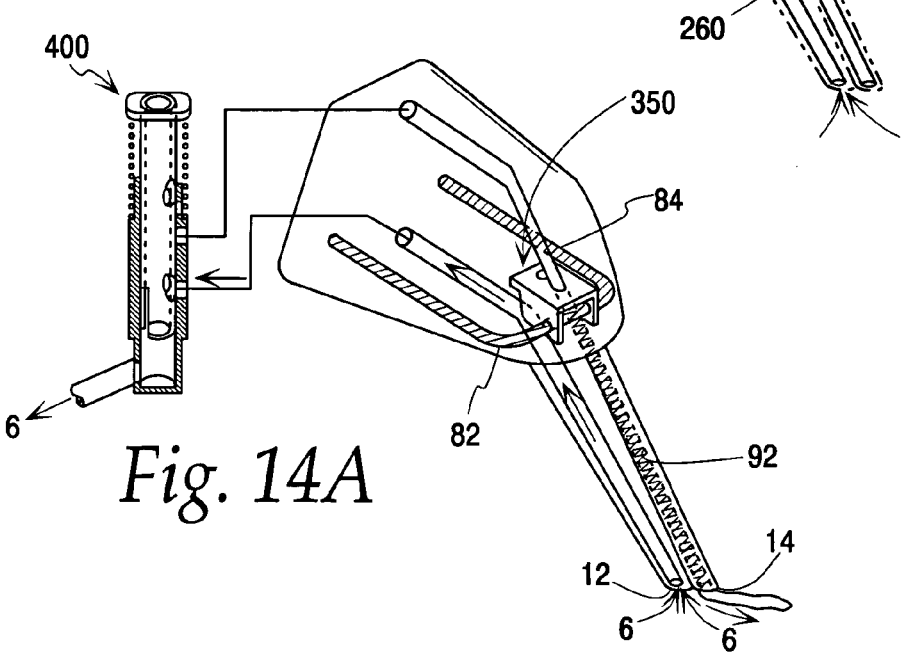

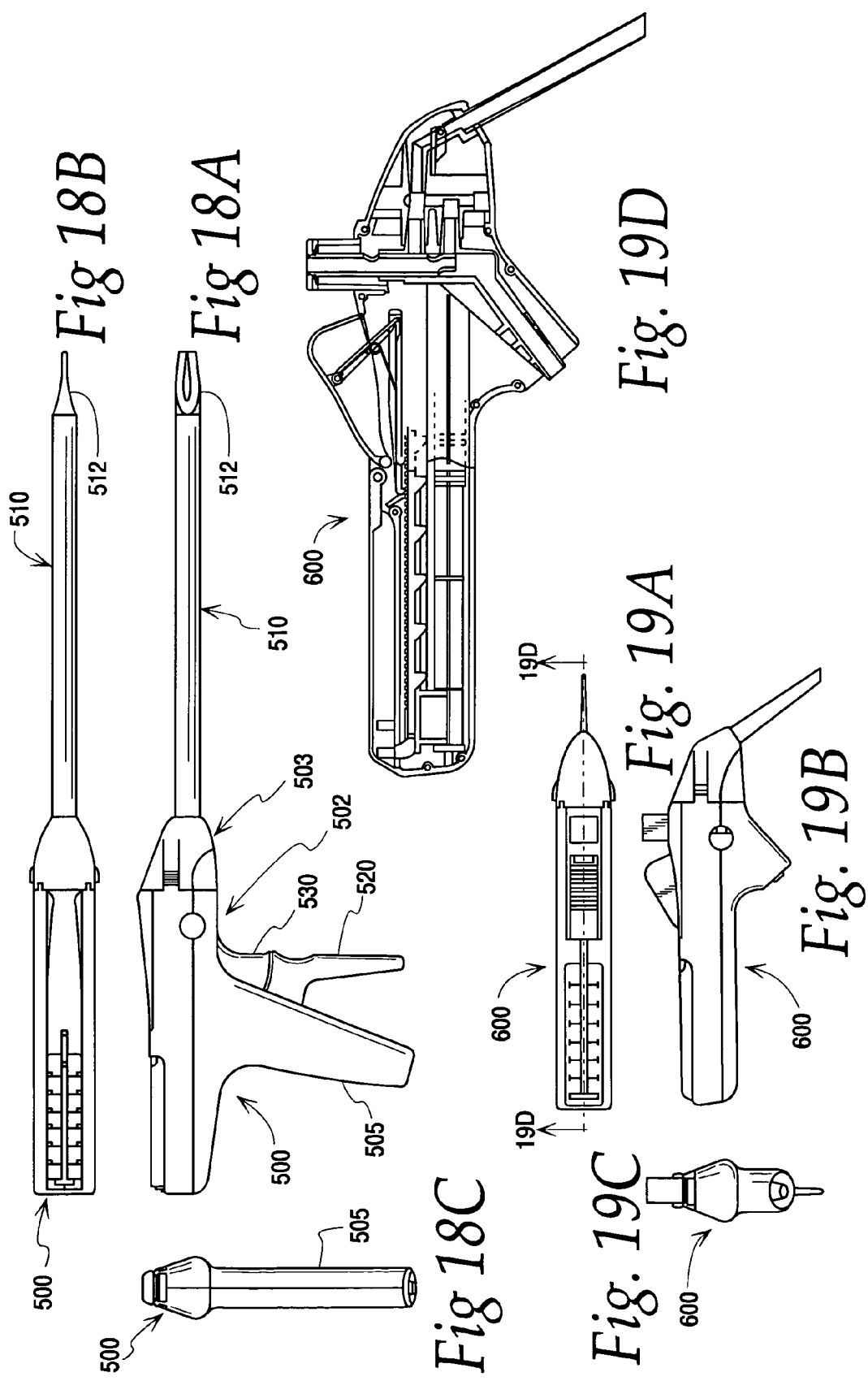

MEDICAL SUCTIONING APPARATUS AND METHODS OF USE

CROSS REFERENCE TO A RELATED APPLICATION

This application is a continuation of patent application Ser. No. 09/421,353 filed Oct. 25, 1999 now U.S. Pat. No. 6,471,667 which is a continuation of patent application Ser. No. 08/839,614, filed Apr. 14, 1997 and entitled "MEDICAL SUCTIONING APPARATUS AND METHODS OF USE," now U.S. Pat. No. 5,971,956, and a division of patent application Ser. No. 08/838,078 filed Apr. 14, 1997 now U.S. Pat. No. 6,331,172 and entitled "APPLICATOR FOR DISPENSING MEASURED QUANTITIES WITH USE OF CONTROLLED SUCTION" the disclosures of which applications are hereby incorporated herein by reference thereto.

TECHNICAL FIELD

The invention is a medical device which provides for controlled levels of applied suction at a device-tissue interface. More specifically, the invention is a medical fluid suctioning device which is combined with a dispensing assembly in an overall tissue adhesive applicator which selectively provides controlled levels of suction force at a suction conduit in the applicator tip during or immediately prior to adhesive application, and which selectively adjusts that suction from the suction conduit to the dispensing conduit for withdrawing coagulated tissue adhesive from the applicator tip.

BACKGROUND

Various medical devices have been disclosed which are adapted to either dispense fluids onto body tissues, suction fluids from body tissues, or to perform a combination of dispensing and suctioning fluids. Examples of such prior disclosure are provided in an overview fashion below.

Various known suction devices have been adapted for different medical applications. In such suction devices, several valve structures have been used to control and vary the amount of suction. These known valve mechanisms for medical suction devices generally: adjust the fluid communication with vacuum directly to the working tip, or alternatively, adjust the proportion of vacuum pressure directed to a vent pathway in parallel with the suction tip. Often, the specific valve structures for adjusting fluid passageways for suction are referred to as stopcock (1,2, or 3-way), gate, pinch, trumpet, or venturi valves.

Examples of suction devices using valve structures which adjust fluid communication directly with the vacuum source are disclosed in U.S. Pat. Nos. 3,645,497; 4,487,600; 4,504, 266. Such devices which also combine fluid dispensing include U.S. Pat. Nos. 2,812,765; 3,208,145; 4,696,669; 4,776,840; 4,891,044; 5,061,180; 5,186,714; 5,295,956; 5,476,450; 5,603,700. Furthermore, such devices that adjust suction in a variably-controlled amount are disclosed in U.S. Pat. Nos. 3,645,497; 4,776,840; and 5,368,560.

One type of mechanism such as that just described is a "pinch valve", such as is disclosed in U.S. Pat. Nos. 4,696, 669 and 5,295,956. U.S. Pat. No. 5,295,956 to Bales et al. discloses a pinch valve providing variable suction control in a hand-held endoscopic suctioning device. In this device, a suction passageway is held closed by a spring-loaded hook (preferably plastic) which is attached to a trigger button. Upon "pulling" the trigger, the attached hook relieves the compression of the flexible tubing, opening the suction passageway. Hence, depending on the displacement of the trigger button, the suction may be controlled.

Similar to pinch valves, trumpet valves also affect fluid communication between the vacuum source and the working tip. Rather than constrict the passageway, however, the trumpet valve functions by controlling the degree of blockage in the suction passageway; thereby adjusting the amount of fluid flowing through the suction passageway.

For example, U.S. Pat. No. 3,645,497 to Nyboer discloses a hand-held variable controlled suction device adapted for use in dental applications. The passageway connecting the vacuum source to the working tip is entirely blocked by a thin plate when the user desires no vacuum pressure. Alternatively, to increase vacuum pressure at the working tip, the user can slide the plate in variable amounts; resulting in an increase or decrease in the amount of fluid flow through the passageway.

A hand-held medical evacuator and irrigation device is disclosed in U.S. Pat. No. 4,776,840 to Freitas. Basically, two ports exist at the working end. One port is directly connected to a vacuum source and the other port either dispenses solution or provides a vacuum. In addition to the constant vacuum port, a second, and adjustable, suction is created by pressing a conveniently located plunger with the user's thumb. By depressing the plunger, the vacuum source communicates with the dispensing port and simultaneously prevents any backflow from contaminating the fluid reservoir. Furthermore, the plunger is tapered which, depending on its displacement, adjusts fluid flow (suction) between the vacuum source and the dispensing port.

In addition to trumpet-type valves, suction may be adjusted by changing the proportion of vacuum pressure directed to a vent pathway in parallel to the working suction tip. These structures are herein referred to as "venturi"-type structures. When the vent pathway is covered, vacuum pressure at the working tip is greatest and all suction is through the passageway. On the other hand, when the vent pathway is open, suction is primarily through the vent pathway and the working tip sees little suction. Furthermore, the amount of vacuum pressure may be adjusted in proportion to the amount of fluid flow through the vent pathway. However, when the working tip is occluded, this control is generally believed to have little sensitivity because most suction flows through the vent pathway.

Examples of venturi-type valves used in medical suction devices are described in the following U.S. Pat. Nos. 3,469, 582; 3,625,221; 4,356,823; 4,445,517; 4,617,013; 4,699, 138; 4,857,047; 5,024,615; 5,226,877. These devices, which also dispense solution, are disclosed in U.S. Pat. Nos. 4,617,013; 4,857,047; and 5,226,877. In U.S. Pat. No. 3,625,221, adjustable venturi suction is disclosed and in U.S. Pat. Nos. 5,419,769 and 3,469,582, a venturi suction actuates another member to communicate fluid flow between the vacuum source and the working tip.

In particular, U.S. Pat. No. 5,024,615 to Buchel discloses a suction device used for surgical operations with a venturi-type valve used to adjust vacuum pressure. The amount of fluid flow through the vent pathway is adjusted by the user's finger-tip and accordingly, the vacuum pressure at the working tip of the device is adjusted.

In addition to trumpet and venturi-type mechanisms described above, another device structure creating mild suction is disclosed in U.S. Pat. No. 5,300,022 to Klapper et al. Here, however, suction is created as an irrigating solution flows across a drainage (vacuum inlet) port at the working tip. Due to the cone shaped structure, the irrigating solution is deflected downward away from the drainage port, creating a mild venturi suction.

In addition to the cited references provided above, further disclosures of suction devices are disclosed in U.S. Pat. Nos. 1,206,126; 3,065,749; 3,949,748; 4,573,979; 4,904,328; 5,024,654; 5,145,367; 5,348,542; 5,433,705.

There is still a need for a medical suctioning device that provides for the controllable selection of varied levels of suction at a working tip.

There is also still a need for a medical suctioning device which inversely and reciprocally adjusts the proportion of applied suction between a suction pathway in a working tip and a vent pathway.

SUMMARY OF THE INVENTION

The present invention is a medical fluid suctioning device which has an applicator tip and a valving means adapted to selectively provide controlled levels of suction pressure at the applicator tip.

In one aspect of the invention, a medical suction device assembly includes a vacuum conduit, a suction conduit, a vent conduit, and a valve manifold adapted to adjust the fluid communication between the vacuum conduit and the suction conduit while simultaneously and inversely adjusting the proportion of vacuum applied to the vent conduit. In this arrangement, a controllable range of applied vacuum at the suction conduit may be selected by varying the proportion of vacuum pressure which is applied between the vent and the suction conduit.

In one variation of this medical suction device assembly, the valve manifold is engaged within a valve housing which includes a vent port in communication with the vent conduit, a suction port in communication with the suction conduit, and a vacuum port in communication with the vacuum conduit. The valve manifold has a valve wall forming a valve chamber and which includes a vacuum aperture, a suction aperture, and a vent aperture. The suction and vent apertures are adapted such that, by varying the positioning of the valve manifold between selected positions within the valve housing, these apertures simultaneously translate across the suction port and vent port, respectively, while the valve vacuum aperture is registered with the vacuum port.

In a further variation, each of the suction and vent apertures also has a non-uniform cross section taken along an elongate axis thereof which is aligned with the axis of motion for translating across the corresponding valve housing port. Each of these two apertures is further positioned on the valve manifold in a relatively reciprocal orientation relative to the other, such that when the valve manifold is adjusted to register an increased-diameter portion of one aperture with its corresponding port, the other aperture has a decreased-diameter portion in registry with the other corresponding port.

BRIEF DESCRIPTION OF THE DRAWINGS

FIG. 1 is an overview perspective view showing one mode of operating an overall medical fluid applicator assembly which includes in part the fluid suctioning device assembly of the present invention.

FIGS. 2A–C are top plan, side elevational, and end elevational views of the medical fluid applicator assembly of FIG. 1.

FIGS. 4A–B are side elevational sectional and top elevational sectional views, respectively, of proximal portions of the fluid dispensing pathway of the medical fluid applicator assembly of FIG. 1, wherein FIG. 4B is taken along line 4B—4B of FIG. 4A.

FIG. 4C is a perspective view of the applicator portion of the assembly of claim 1, further showing a dispensing conduit in shadowed view as the distal end portion of a fluid dispensing pathway.

FIG. 5 is an elevational sectional view of the dispensing assembly of the medical fluid applicator assembly of FIG. 1, taken through the center of the device along line 5—5 of FIG. 2A.

FIG. 6 is a top plan view of a rack used in an actuating assembly and in an audible volume indicator included in the medical fluid applicator assembly of FIG. 1.

FIG. 7 is a top plan view of the plungers used with the rack in the actuating assembly of the medical fluid applicator assembly of FIG. 1.

FIGS. 9A–E are top elevational, bottom elevational, side elevational sectional, user end elevational, and working end elevational views, perspectively, of the valve stem used in a valve manifold of the suction assembly shown in FIG. 8, wherein FIG. 9C is taken along line 9C—9C of FIG. 9A.

FIGS. 10A–D are top elevational, bottom elevational, and two side elevational sectional views, respectively, of the valve actuator used to actuate the valving of the suction assembly of FIG. 8, wherein FIG. 10C is taken along line 10C—10C and FIG. 10D is taken along line 10D—10D of FIG. 10A.

FIGS. 11A–D are top plan, side elevational, side elevational sectional, and end elevational sectional views, respectively, of a shuttle valve which coordinates dispensing and clearing mechanisms of a dispensing conduit provided in the overall medical fluid applicator of FIG. 1, wherein FIG. 11C is taken along line 11C—11C of FIG. 11A, and FIG. 11D is taken along line 11D—11D of FIG. 11B.

FIGS. 12A–C are exploded side elevational sectional views of the suction assembly of FIG. 8, showing a valve stem in three sequential positions within the valve manifold housing which correspond to an open vent pathway, an open suction pathway, and an open clearing pathway, respectively.

FIGS. 13A–B are schematic representative views of the valve manifold of the current invention during sequential modes of operation, respectively, in selectively and controllably adjusting the amount of applied suction to the suction pathway of FIG. 12B.

FIGS. 14A–B are schematic representative views of the valve manifold during sequential modes of operation, respectively, in shuttling applied vacuum from the suction pathway of FIG. 12B during fluid application to the clearing pathway of FIG. 12C following fluid application, respectively.

FIGS. 18A–C are side perspective, top perspective, and user end perspective views, respectively, of further actuating trigger and applicator tip variations adapted for moderately invasive surgery applications of the medical fluid applicator variation of the current invention.

FIGS. 19A–D are top perspective, side perspective, end perspective, and sectional perspective views of a medical fluid applicator of the present invention with a further variation in the conduit lumen arrangement at the applicator tip portion, wherein FIG. 19D is taken along line 19D—19D of FIG. 19A.

DETAILED DESCRIPTION OF THE INVENTION

Figure 3:
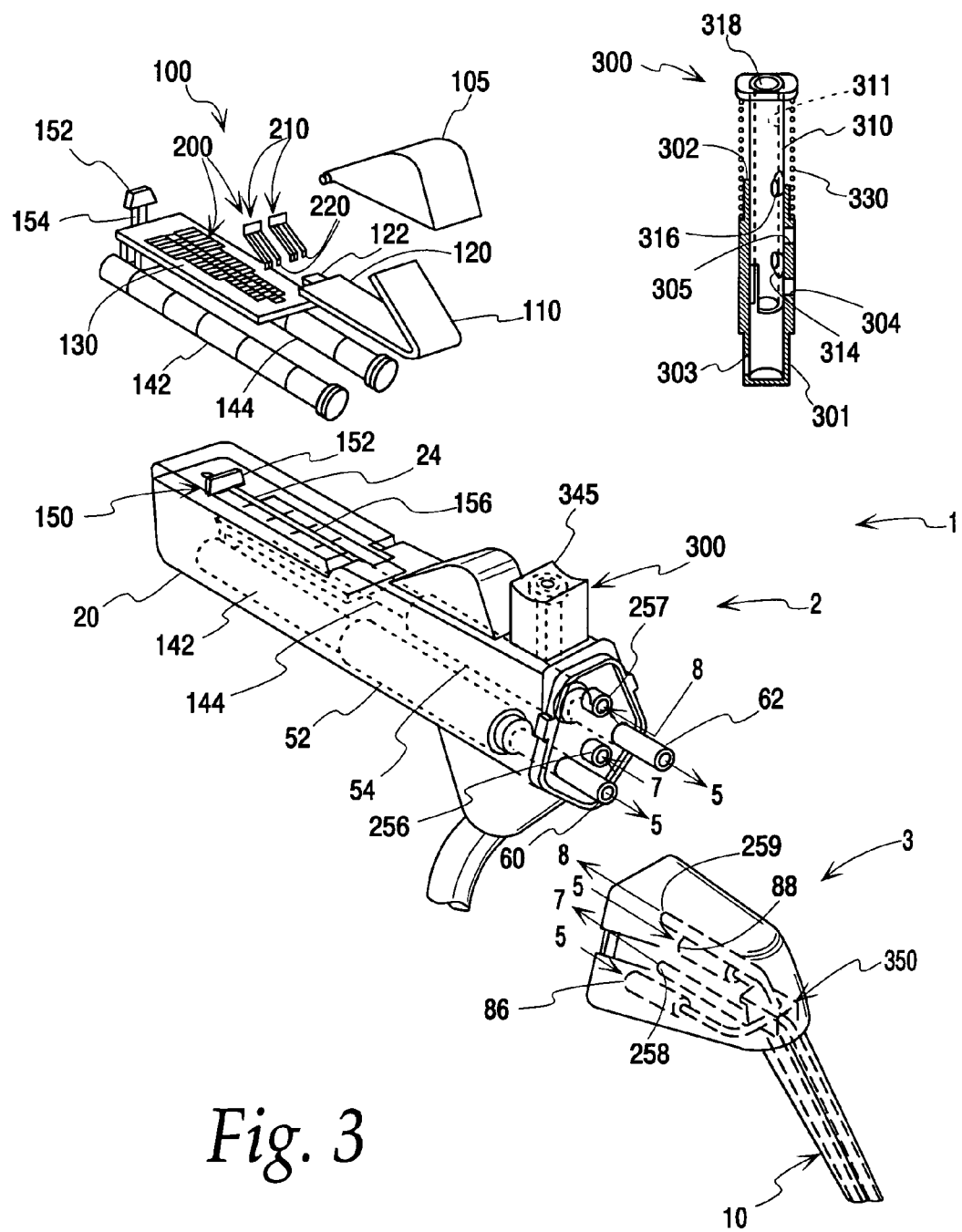
FIG. 3 is an exploded perspective view of the medical fluid applicator assembly of FIG. 1, showing an applicator portion removed from a supply device portion, and further showing the internal structure of the respective portions in shadow, as well as exploded schematic views of portions of an actuating assembly, an audible volume indicator, and a valve manifold included in the fluid suctioning device assembly of the present invention.

The present invention will be illustrated by means of a preferred embodiment shown in the drawings. The medical fluid suctioning device of the present invention is useful as a stand alone suctioning device. However, it is to be appreciated by the illustration and description below of one preferred embodiment that the suctioning invention is useful in combination with various features of a dispensing assembly to form an overall medical fluid applicator.

Detailed description of the suctioning device of the present invention is therefore provided as one part of an overall disclosure of the preferred mode of operation in a combination medical fluid applicator device having several assemblies and sub-assemblies described. FIGS. 1–2C provide various perspective views of the overall combination medical fluid applicator assembly. FIG. 3 provides an overview of the removably engageable supply device and applicator portions of the overall device, as well as the overall interior workings of the dispenser and the suction assemblies of the device. FIGS. 4–7 provide increasing detail regarding the dispenser assembly aspects of the present invention. FIGS. 8–14 provide increasing detail regarding the suction assembly of the present invention, including step-wise views of the various suctioning and clearing modes of operating the suction assembly. FIGS. 15–17E provide increasing detail regarding the filling dispenser aspects of the present invention. FIGS. 18A–20C provide various views of alternative applicator tips which are believed to be useful in performing particular types of medical procedures with the overall medical fluid applicator variation of the present invention.

Referring to a general overview of the device by reference to FIGS. 1–2C, medical fluid applicator assembly (1) is shown in overview fashion in FIG. 1 during one mode of operation as a tissue adhesive or sealant applicator. Applicator tip (10) of the device is shown with an arrow as it is withdrawn across a tissue surface (not shown) such that the tip suction aperture (12), which is coupled to a vacuum source, leads the tip dispensing aperture (14), which is coupled to a tissue adhesive source, across the tissue surface. In this manner, vacuum applied to the tip suction aperture (12) aspirates fluids from the tissue to thereby prepare the tissue for fluid application. As the tip dispensing aperture (14) translates across the tissue surface immediately behind tip suction aperture (12), a trail of tissue adhesive (16) is dispensed onto the prepared tissue.

It is believed that a close proximity in time between tissue preparation and fluid application has a particularly useful application in dispensing tissue adhesives onto tissue surfaces in wound closure procedures. It is further believed that the sensitive ability to select levels of applied suction, as provided by the present suctioning device invention, beneficially allows for desired control in preparing the tissue, aspirating overflow of dispensed fluid, and manipulating tissue to proximate the dispensing tip. As would be apparent to one of ordinary skill, the remaining detailed disclosure below describes additional operating features of the overall medical fluid applicator embodiment, as well as additional specific features of the novel suctioning assembly of the current invention, in addition to the features shown in FIG. 1 which provide for tissue preparation contemporaneous with fluid application.

As shown in FIG. 3, the inner workings of medical fluid applicator (1) in one preferred variation are divided between supply device portion (2) and applicator portion (3) which is removably engageable to supply device portion (2). As is apparent to one of ordinary skill by reference to FIG. 3, when applicator portion (3) and supply device portion (2) are engaged, proximal and distal portions of a fluid dispensing pathway (5), a suction pathway (7) and a clearing pathway (8) are coupled, respectively. These pathways thereafter allow for fluid dispensing, applied suction, and clearing of the applicator tip, respectively, as will be apparent to one of ordinary skill from the more detailed description provided below.

The various components of the dispenser assembly to be combined with the current suctioning assembly of the current invention are generally shown in FIGS. 3–7. In this variation, the dispenser assembly includes an overall dispensing pathway (5), the proximal portions of which being shown in detail in FIGS. 4A–C, as well as an actuating assembly (100) for dispensing fluid through that pathway, shown in detail in FIGS. 5–7.

Regarding the components of the fluid dispensing pathway (5) as shown various throughout FIGS. 3–4C, proximal portions of that pathway within the supply device portion are shown in FIGS. 4A–B to include two reservoirs (52,54) which communicate with two supply conduits (56,58), respectively. Supply conduits (56,58) extend distally therefrom and terminate distally in two supply ports (60,62), respectively.

It is to be further appreciated by one of ordinary skill that the reservoirs of the fluid dispensing pathway can take a number of forms as long as they are adapted to contain the desired fluid, are pressurizable by an engaged actuating mechanism, and are coupled to a dispensing conduit for distal flow. In the embodiment shown throughout the figures, the reservoirs are tubular chambers which are pressurizable as syringes by means of slideably engaged plungers. In an alternative embodiment not shown, the reservoir may instead comprise a flexible bulb or tube that may be directly compressed, which compression may also be accomplished by means of a plunger. Any suitable arrangement whereby the application of pressure to the reservoir attached to the dispensing means will result in application of the contained fluid is acceptable.

Distal portions of fluid dispensing pathway (5) located within applicator portion (3) are shown in shadow in FIG. 4C. Here, dispensing conduit (70) has a branched portion (80) and a mixed portion (90) that resides in part within applicator tip (10). Branched portion (80) includes two branched conduits (82,84) which terminate proximally in proximal dispensing ports (86,88), respectively. The branched conduits (82,84) merge at the proximal end of mixed conduit (92), which extends distally therefrom through applicator tip (10) where it terminates at tip dispensing aperture (14).

Therefore, it should be apparent to one of ordinary skill by reference to FIGS. 3–4C that fluidly coupling supply ports (60,62) and dispensing ports (86,88) at the supply device/applicator portion interface creates interface fluid dispensing pathway (5) which includes reservoirs (52,54), supply conduits (56,58), branched conduits (82,84), and mixed conduit (92).

Actuating assembly (100) is also shown in overview fashion in FIG. 3, with more detailed reference to the components thereof provided with reference to FIGS. 5–7.

In overview, actuating assembly (100) includes trigger (105) which is mechanically coupled to two parallel plungers (142,144), which are in-turn coupled to fluid dispensing pathway (5) via slideably engagement within reservoirs (52,54), respectively. By manually depressing trigger (105), plungers (142,144) advance within reservoirs (52,54) to thereby pressurize the fluids and dispense them distally therefrom and through the remaining portions of fluid dispensing pathway (5).

Referring to the detail of actuating assembly (100) shown in FIGS. 5–7, trigger (105) is coupled to pawl (120) via lever arm (110). Spring (115) is further shown with one end engaged with lever arm (110) and the other end engaged with pawl (120). In this arrangement, both trigger (105) and pawl (120) have a spring bias such that trigger (105) has a first resting position and pawl (120) has a reward resting position. Pawl (120) is further shown in FIG. 5 to include a hook (122) which has a flat distal face (124) and a radiused proximal face (126). Hook (122) functions to engage rack (120) with rack (130).

Rack (130) is further shown in FIGS. 5–6 to include a rack face having a plurality of teeth (132) which border either side of a longitudinal groove (133) extending along that rack face. These teeth (132) are longitudinally spaced with a gap (134) which is adapted to receive hook (122), each tooth including a radiused distal face (136) and a flat proximal face (138). At the proximal end of rack (130), engaging arm (139) is shown as a branched arm extending downwardly to engage at least one of plungers (142,144).

The actuating assembly shown and described further includes a decoupling mechanism, which is shown in-part in FIGS. 5 and 6 (not included in the view of the dispensing assembly shown in FIG. 3). A narrow decoupling arm is shown in FIG. 5 as a longitudinal extension of tab (152) and includes a plurality of sloped cam surfaces (131) which resides within rack (130) and which rest on a bottom face of the rack in confronting engagement with a plurality of sloped decoupling surfaces, such as sloped decoupling surface (135). The decoupling arm may be adjusted upwardly through the upper face of the rack through longitudinal groove (133) by moving the decoupling arm proximally within the rack to allow the arm to be lifted by the sloped decoupling surfaces. The decoupling arm is further limited in its longitudinal motion within the rack such that the tab engaged to the arm may be used to withdraw the rack, and therefore the plungers engaged therewith, proximally within the outer casing of the device housing.

Each of plungers (142,144) of actuating assembly (100) (FIG. 5) includes a proximal shaft and a distal head, as is shown by example at proximal shaft (146) and distal head (148) in FIG. 7. Plungers (142,144) include a plurality of splines (147) which are spaced in order to receive and mechanically engage engaging arm (139) therebetween. Distal head (148) is configured of geometry and material to slideably but frictionally engage the interior wall of one of the fluid reservoirs. As such, distal head (148) is adapted to slide within the corresponding reservoir during forward advancement of the plunger in order to pressurize the fluid within that reservoir. Yet, distal head (148) is also adapted to be frictionally in contact with the reservoir's inner bore in order to prevent backflow of the pressurized fluid. In one variation, an elastomeric member such as an O-ring may be included, such as O-ring (149) shown in FIGS. 5 and 7.

Closely integrated with the operation of actuating assembly (100) are visual volume indicator (150) and audible volume indicator (200), as shown in overview fashion in FIG. 3.

Visual volume indicator (150) is shown in FIG. 3 and also in FIG. 5 to include a tab (152) which rests above the housing of the device which is shown as outer casing (20). Tab (152) is coupled to lower arm (154) that extends downwardly through longitudinal groove (24) (FIG. 3) in the upper surface of outer casing (20) and is further engaged to rack (130). Visual graduations (156) are provided on the upper surface of outer casing (20), which graduations correspond the relative position of tab (152) to known volumes of fluid delivery.

The mechanism of an audible volume indicator (200) is herein described also by reference to FIG. 3, as well as to FIGS. 5 and 6. Audible volume indicator (200) includes a striker (210) which is actuated by teeth (132) to emit audible tones of varying pitch or loudness as fluid is cumulatively dispensed over a range of discrete, incremental volumes of fluid. Striker (210) is secured to the interior of outer casing (20) with fixed positioning relative to the longitudinal motion of rack (130) and includes a plurality of striker arms (220) (FIG. 3) which are spaced laterally across the face of rack (130).

Teeth (132) are further shown to include various regions along the longitudinal axis of rack (130), such as regions (137,139) shown in FIG. 6. Each region has a unique lateral position on the rack relative to the adjacent regions and is thereby adapted to strike a unique combination of laterally spaced striker arms (220) when advanced distally across striker (210), as would be apparent to one of ordinary skill. The distance between the leading edges of each region generally corresponds to an incremental distance of longitudinal travel for rack (130) relative to striker (210) with fixed relative positioning. This incremental distance of travel for rack (130) further corresponds to a predetermined, incremental volume of actuated fluid delivery. Therefore, this arrangement allows for a unique tone to be emitted from a unique combination of striker arms (220) at each discrete, incremental volume of fluid delivered. Therefore the cumulative volume of fluid delivered is recognized by the unique loudness or pitch of emitted tone since the extent of forward positioning of rack (130) within outer casing (20) corresponds with a specific regions of teeth (132) that strike unique combinations of striker arms (220).

It is to be further understood by one of ordinary skill that the particular mechanism disclosed for varying the pitch or loudness of audible signals should not limit the breadth of scope for the present invention. For example, in the embodiment shown, striker arms (220) are shown to be relatively uniform in size and geometry and the various regions of teeth (132) are shown to simply vary in length while sharing common central regions which may engage some of striker arms (220). In this arrangement, it is the number of actuated striker arms (220) which varies with the tooth regions, which corresponds to a change in the loudness of the tone emitted for each region. However, other arrangements may also be suitable. In one alternative embodiment not shown, the geometry or material of the striker arms may vary along the striker, wherein each unique arm may emit a uniquely pitched tone. In combination, the teeth regions may be as shown in the figures with common striking portions, or may be shifted to only actuate audible signals from entirely unique sets of teeth, as would be apparent to one of ordinary skill.

Moreover, other mechanisms than the rack teeth mechanism shown and described may be suitable for varying the tone or pitch of an audible signal as fluid delivery is actuated. For example, the teeth may be fixed within the casing of the device, with the striker translating across those teeth as an actuator delivers fluids. Alternatively, the teeth might be positioned along a helical path of a screw, the striker being adapted to engage that path and thereby actuated for tone emission by the teeth there.

Still further, other mechanisms than the shown teeth/striker mechanism may be acceptable, such as an optical or electronic reader which observes changing indicia of actuated fluid delivery and which is thereby coupled to an electronically or electrooptically actuated audible signaling means, as may be apparent to one of ordinary skill. In any case, any variation which audibly emits signals as indicia of cumulative volume of fluid delivery should be considered as a part of the current invention.

The operation of the dispenser assembly used with the current invention is also shown in two modes in FIG. 5, wherein actuating assembly (100) is shown actuated through one full range of motion or "stroke" of actuating trigger (105). As is evident to one of ordinary skill by reference to FIG. 5, depressing trigger (105) through one stroke actuates forward movement of pawl (120) from a reward resting position to a forward actuated position (shown in dashed line). This motion is achieved by flat distal face (124) of hook (122) confronting the flat proximal face (138) of teeth (132) such that the forward movement of pawl (120) pulls rack (130) forward. As rack (130) pulls forward, plungers (142,144) engaged to rack (130) are also actuated to move forward into the bore of the fluid reservoirs, as is shown at fluid reservoir (52). As the fluid in the reservoirs are pressurized with the forward motion of plungers (142,144), that fluid is dispensed distally through the fluid dispensing pathway, originating from the reservoirs and flowing from the supply device portion and into the applicator portion through supply ports.

The dispenser assembly shown and described for the current invention is filled (or refilled after completion of fluid dispensing) as follows. Filling is initiated with the rack and the plungers in a fully forward and actuated position. The tab engaged to the rack and to the narrow decoupling arm also has a forward position. The device is coupled to a filling dispenser, such as the novel filling dispenser shown and described with reference to FIGS. 15–17E below. The tab is then manually withdrawn through the longitudinal groove in the outer casing of the supply device. By doing so, the cam surfaces on the bottom face of the disengaging arm slide across the decoupling cam surfaces on the bottom face of the rack until reaching the stop within the rack, thereby lifting the disengaging arm upwardly through the longitudinal groove in the upper face of the rack to lift the hook of the pawl and disengaging it from the teeth on the rack surface. Continued proximal movement of the tab relative to the outer casing of the device also pulls the plungers and the rack rearwardly to create a vacuum to fill the reservoirs and to also reposition the rack proximally so the hook on the pawl returns to the front part of the rack.

The spring-biased resting position of trigger (105) further corresponds to a rearward or proximal position for pawl (120) relative to the longitudinal axis of outer casing (20). When the trigger (105) is released, spring (115) restores the trigger and also the pawl to their original position, while the striker remains in its advanced position along the regions of the teeth on the forward actuated rack. Moreover, the spring-bias and mechanical constraints on the motion of lever arm (110) and pawl (120) within outer casing (20) also limit the range of available motion for trigger (105) from the spring-biased resting position to a fully actuated position, thereby defining the full "stroke" range. The combined features of the overall actuating assembly are adapted such that the available "stroke" range of actuated motion corresponds to a predetermined incremental volume of fluid delivery actuated from the fluid reservoir.

Moving to the suction assembly of the current invention, FIG. 3 provides an overview of the overall suction assembly, while FIGS. 5 and 8–12C provide increasingly more detail of the components and mechanisms of operation thereof.

Figure 8:
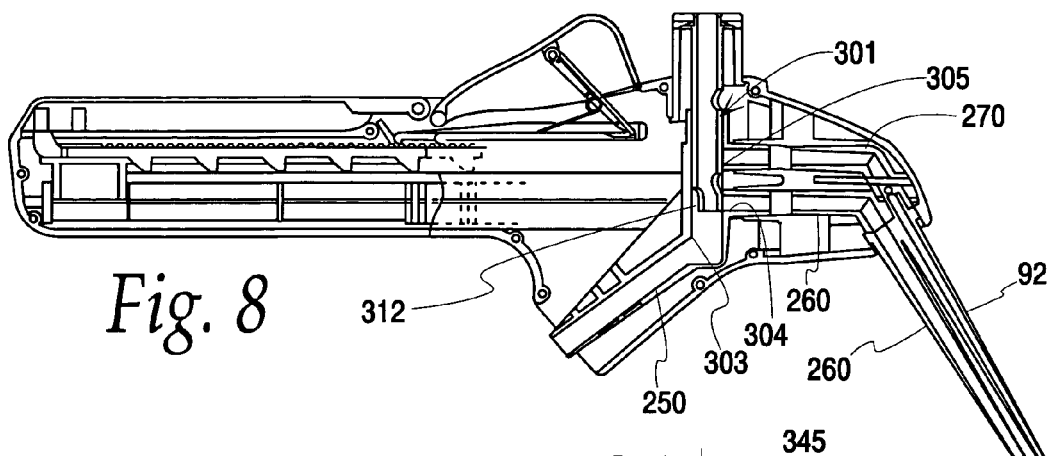
FIG. 8 is a similar elevational sectional view of the medical fluid applicator assembly as shown in FIG. 5, although showing both the supply device portion and the applicator portion in sectional view to show the suction assembly of the current invention.
Figure 9A:
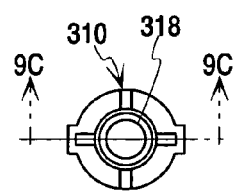
Figure 10A:
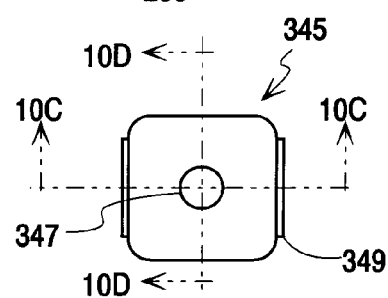
Figures 9C, 9D, 9E:
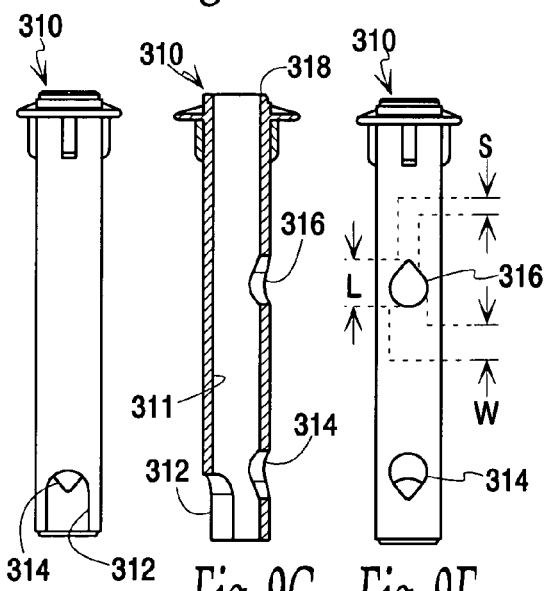
Figures 10C, 10D:
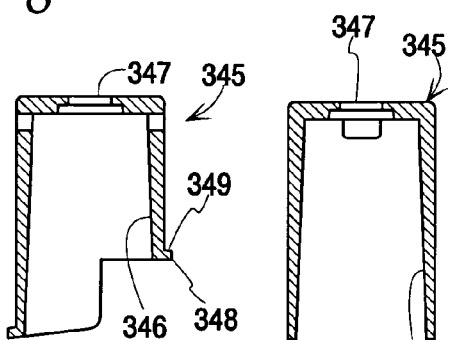
Figure 9B:
Figure 10B:
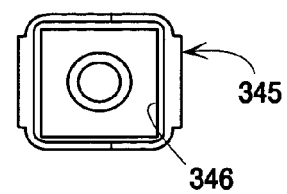

The proximal portions of the suction assembly located within supply device portion (2) are shown in FIG. 5 to include a vacuum conduit (250) which is selectively coupled to vacuum coupling ports (256,257) by vacuum manifold (300). The distal portions of the suction assembly located within applicator portion are shown in FIG. 8 and include a suction conduit (260), a clearing conduit (270). Comparing the overall device assembly shown in FIG. 8 with the removed view of supply device portion (2) and applicator portion (3) in FIG. 3, it should be apparent to one of ordinary skill that clearing conduit (270) is formed by coupling and aligning supply device suction port (256) with applicator suction port (258), and similarly coupling and aligning supply device clearing port (257) with applicator suction port (259) (FIG. 3) to form one contiguous channel between the valve housing and the mixed portion of the dispensing conduit.

FIGS. 11A–D and 14A–B further show a shuttle valve (350) which is further included in the distal portion of the suction assembly for adjusting applied vacuum between the suction conduit (260) and the clearing conduit (270). As will be disclosed in further detail below, the valve manifold (300) operates to adjust the proportions of applied vacuum from the vacuum conduit (250) to either the suction conduit (260), when suction at for tissue preparation prior to dispensing, or to the clearing conduit (270), when suction is desirably used to clear coagulated tissue adhesive proximally from the mixed portion (90) of dispensing conduit (70).

The operable features of valve manifold (300) are shown in FIG. 8, and include valve housing (301) which houses valve stem (310) in moveable engagement.

Valve housing (301) is shown in FIG. 8 to form an elongate bore having an open top in communication with atmospheric pressure and which functions as a vent port (302). Furthermore, the wall forming the inner bore of valve housing (301) further includes a suction port (304) and a clearing port (305) on the distal side of valve housing (301). Vacuum port (303) communicates with vacuum conduit (250), while suction port (304) and clearing port (305) communicate with vacuum coupling ports (256,257), respectively.

Valve stem (310) is shown variously in FIGS. 3, 5, and 8, and in more detail in FIGS. 9A–D, and generally includes a valve chamber (311), a vacuum aperture (312), a suction aperture (314), a clearing aperture (316), and a vent aperture (318), which apertures are shown in detail in FIGS. 9A–D. Valve stem (310) is generally an elongate tubular member which has an outer diameter adapted to frictionally engage the inner surface of valve housing (301)(FIG. 8). Valve stem (310) is also slidable within valve housing (301), however, and is thereby adjustable between various positions along a predetermined range of motion. According to the embodiment shown throughout the figures, valve stem (310) has a vertical range of motion within valve housing (301) in order to adjust the relative positioning of the various valve apertures for selective registry with the various ports in the valve housing, as will again become more apparent with reference to FIGS. 12A–14B below. This range of motion is in part limited by the spring which also gives the valve stem a spring-bias in the upward resting position where there is no applied suction.

More detailed description of the various valve apertures and parts as shown in FIGS. 8 and 9A–E is as follows. Vacuum aperture (312) includes an open bottom of valve stem (310) and also an elongate open slot on the proximal side of valve stem (310). Suction port (314) and a clearing port (316) which are positioned at particular respective positions along a common vertical plane of valve stem (310). In addition, valve stem (310) further includes an open vent aperture (318) which selectively communicates exteriorly of valve chamber by manually covering or uncovering that opening.

Further to the design of valve stem (310) and its apertures as shown in FIGS. 9A–D, each of suction aperture (314) and clearing aperture (316) is shown to be a non-circular shaped opening having an elongate axis aligned with the longitudinal axis of valve stem (310) (shown in dashed line in FIG. 9E), a wide axis, and a short axis, such as are shown at long axis "L", wide axis "W", and short axis "S" for clearing aperture (316). Wide axis "W" has a larger cross-sectional area than the cross-sectional area of short axis "S" in the perpendicular plane to long axis "L". For the purpose of further understanding, this described shape may be considered a "tear-drop" shape, or a "diminished elliptical" shape. In addition, the wide and short axes of clearing aperture (316) are provided in an inverse reciprocal orientation along the longitudinal axis relative to the respective orientation of suction aperture (314). The primary purpose for this inverse reciprocal orientation of long and short axis for suction aperture (314) and clearing aperture (316) is in one particular mode of operation wherein clearing aperture (316) is used as a vent in a venturi valve-role for controlling the level of suction applied to suction conduit (270), as will be developed further below with reference to FIGS. 13A–B. Nevertheless, it should be apparent to one of ordinary skill that the short axis leads the wide axis for suction aperture (314) during a downward vertical motion of valve stem (310) along its longitudinal axis, while the wide axis instead leads the short axis for clearing aperture (316) during that range of motion.

A valve actuator (345) is further shown in FIGS. 3, 5, and 8, and in further detail in FIGS. 10A–D. Valve actuator (345) can be considered to be a part of the overall assembly for valve manifold (300), as well as for a shuttle valve used in a further variation of the present invention, as will be developed below. Valve actuator (345) is generally a button which has a button bore (346) that is adapted to fit over valve stem (310) such that actuator vent aperture (347), which is provided at the top surface of valve actuator (345), is adapted to align with vent aperture (318) of valve stem (310) when engaged to the top of the valve stem. Near the bottom region of valve actuator (345) is a cam actuator surface (348) which includes at least one stop, such as that shown at stop (349). Cam actuator surface (348) is adapted to engage a cam surface of a shuttle valve when valve manifold (300) is adjusted toward downward position within valve housing (301) in order to actuate movement of the shuttle valve to initiate a suction clearing operation, which will be developed below with reference to FIGS. 14A–B.

FIGS. 11A–D show shuttle valve (350) which is adapted to be actuated by valve actuator (345) (FIGS. 10A–D) for use in a clearing mode of operating the suctioning assembly of the current invention in the preferred medical fluid applicator design. Shuttle valve (350) functions to selectively and alternatively couple the mixing conduit portion of the dispensing conduit either to the branched portion for dispensing fluids or to the clearing conduit for retrogradedly clearing clogged adhesive from the mixing conduit.

Shuttle valve (350) is shown in FIGS. 11A–D to include a body (352) which includes a dispensing valve portion (360), a clearing valve portion (370), and a proximal portion having a cam surface (380). Dispensing valve portion (360) includes two vertical splines (362,363) which are parallel to the longitudinal axis (dashed line) of shuttle valve (350). Vertical splines (362,363) have dispensing conduit apertures (364,365), respectively, which extend therethrough in a transverse horizontal plane relative to the longitudinal axis. Vertical splines (362,363) further have closed regions which are adjacent the corresponding dispensing conduit apertures, such as is shown in FIG. 11B at closed region (366) for vertical spline (362) and in FIG. 11C at closed region (367) for vertical spline (363). Clearing valve portion (370) includes a horizontal face (372) which extends between vertical splines (362,364) and which further includes a clearing conduit aperture (374) therethrough in an angled vertical plane relative to the longitudinal axis. At least one seal member (390) is further shown to be disposed upon the outer surface of the respective valve portions, which seal member is preferably an elastomeric or compressible material, such as an elastomeric polymer or a rubber.

The means for actuating shuttle valve (350) in order to operate the suction shuttling in the clearing variation of the present invention is further shown in FIGS. 11B–C. Cam surface (380) is disposed on an angled vertical plane relative to the longitudinal axis of shuttle valve (350). In this orientation, cam surface (380) is adapted to slideably engage cam actuator surface (348), as is further shown in FIG. 11C. As the valve actuator (345) is depressed in a downward motion, cam actuator surface (348) contacts cam surface (380). Further downward motion of valve actuator (345) forces shuttle valve (350) to advance transversely to the motion of valve actuator (345) and in the longitudinal plane of shuttle valve (345). This is because shuttle valve (345) is restricted from moving within the applicator tip in all directions except longitudinally. The angled interaction between cam actuator surface (348) and cam surface (380) provides the longitudinal component of normal force therebetween to actuate the longitudinal shuttling motion.

Further included in the shuttle valve mechanism of the present invention is a spring bias on the shuttle valve in a rearward resting position, such as by use of a spring which is engaged to the shuttle valve and also to the interior of the applicator portion of the device housing (not shown). The forward actuated movement of the shuttle valve by operation of the actuator works against that spring bias such that upon releasing the actuator the shuttle valve returns to the rearward position.

Figure 12B:
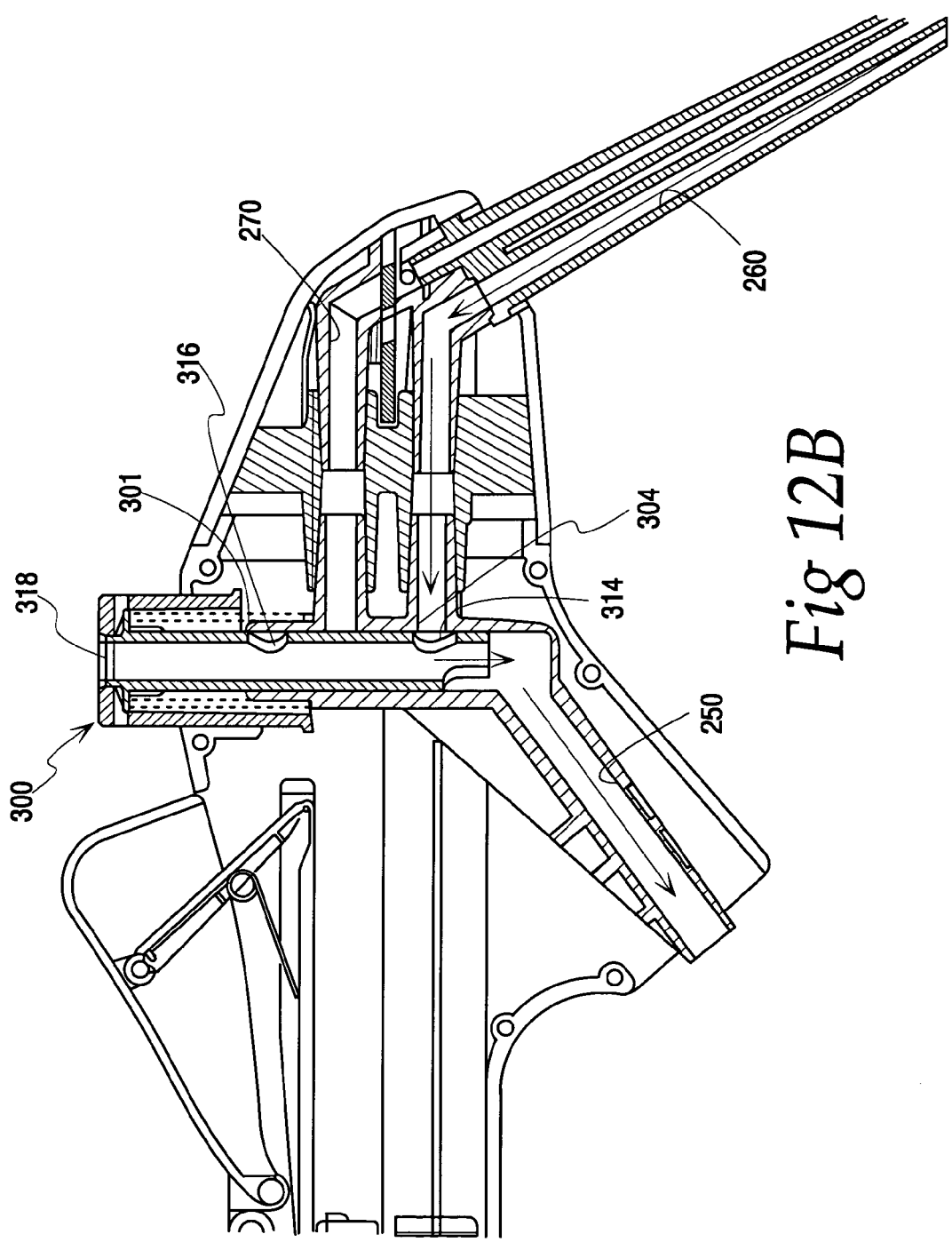
Figure 14B:
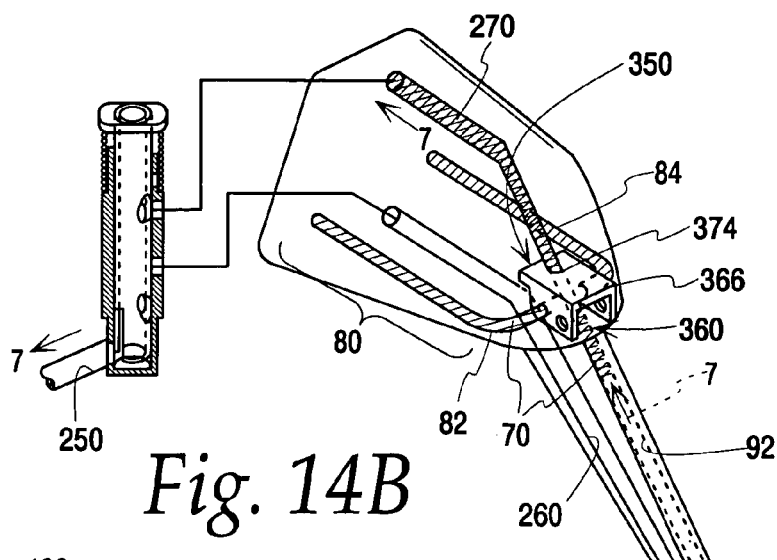

The operation of the valving components of the present suctioning invention, including the valve manifold and the shuttle valve (in the clearing variation), is shown in various modes of operation throughout FIGS. 12A–14B. FIGS. 12A–12C show the relationship of the various positioning of valve manifold (300) in the creation of different pathways for suction through the various available conduits. FIGS. 13A–B schematically shown the positioning of valve manifold (300) and shuttle valve (350) during different modes of venting and suctioning operations at the applicator tip. FIGS. 14A–B show different positions for valve manifold (300) and shuttle valve (350) in the creation of an alternative clearing pathway for applied suction through the clearing conduit to clear the mixed portion of the dispensing conduit.

FIG. 12A shows valve manifold (300) in a venting position such that a vent pathway (4)(bolded arrows) is created and there is no applied suction to suction conduit (260) or clearing conduit (270). In this position, vacuum conduit (250) communicates with valve chamber (311) which is exposed only to atmospheric pressure through vent aperture (318) and the coupling between clearing aperture (316) and vent port (302) above valve housing (301). In this case, clearing aperture (316) functions as another vent aperture. As is apparent in FIG. 12A, this venting position is the resting position for valve manifold due to a spring bias to that position created by spring (330) as stop (349) engage portions of interior surface of outer casing (20).

FIG. 12B shows valve manifold (300) in a first suction position such that a suction pathway (6) is created by registering suction aperture (314) with suction port (304). In this position, vacuum conduit (250) communicates with suction conduit (260) to apply vacuum pressure to that suction conduit in the suction pathway (6). Further, clearing aperture (316) is closed within valve housing (301) and a user's thumb functions to close vent aperture (318) during downward actuation of the valve manifold (300). By maintaining these apertures in a closed condition, the suction pathway (6) is isolated to achieve full vacuum at the applicator tip.

Figure 12C:
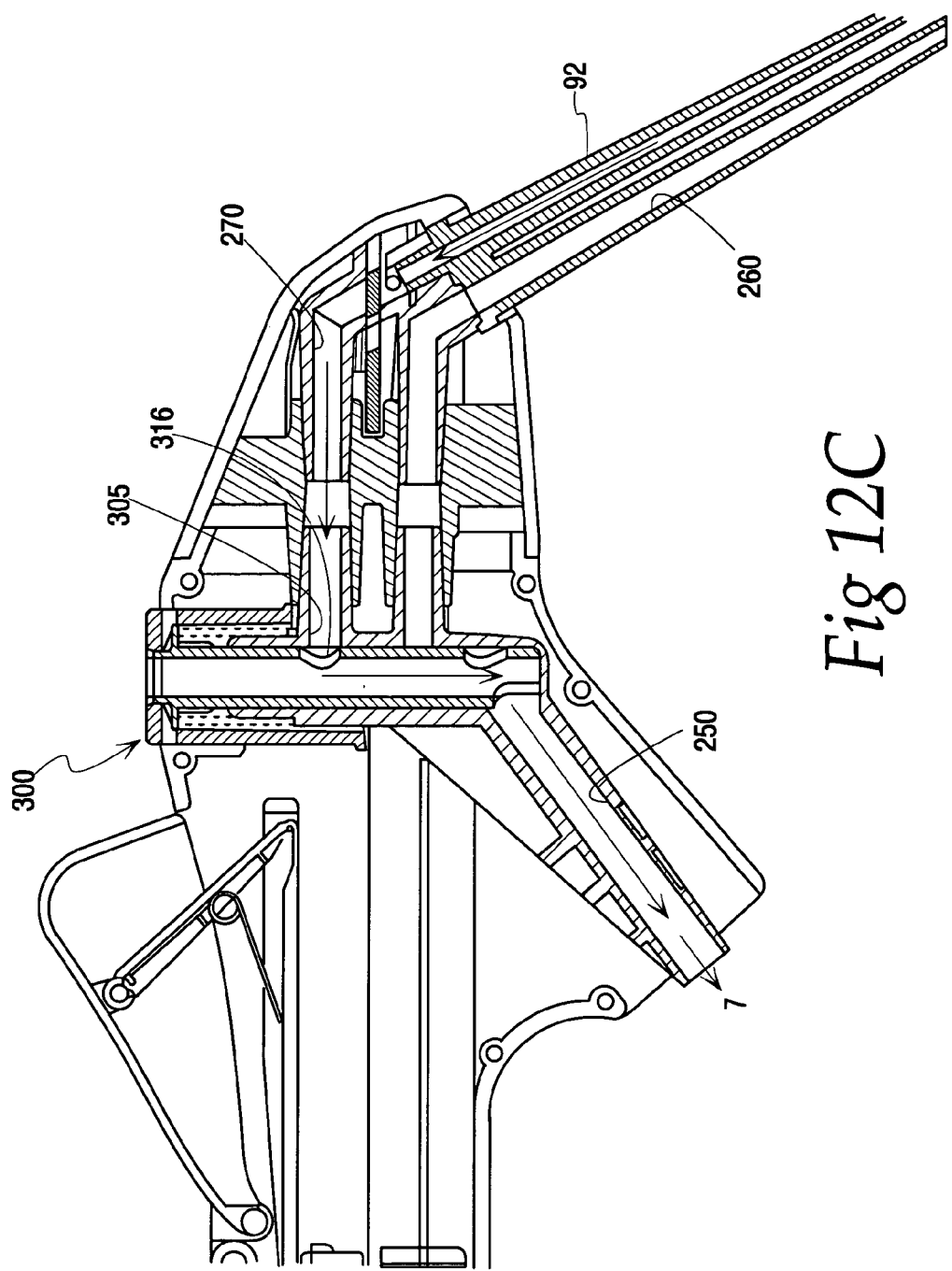

FIG. 12C shows valve manifold (300) is a second clearing position such that a clearing pathway (7) is created by registering clearing aperture (316) with clearing port (305). In this position, vacuum conduit (250) communicates with clearing conduit (270) to apply vacuum pressure to that clearing conduit through clearing pathway (7). The completion of clearing pathway (7), however, is intended to include mixed conduit (92), in order to achieve the intended operation of clearing clogging obstructions from that conduit. This coupling to the dispensing conduit is achieved through the actuation of the shuttle valve, as will be described in more detail with reference to FIGS. 14A–B.

As shown in FIG. 12C, the clearing conduit (270) is coupled to the proximal end of the mixed conduit (92) such that a continuous taper is created with distally reducing inner diameter between those conduits. It is believed that this tapered geometry may enhance the retrograde passing of contents within mixed conduit (92) due to applied suction, particularly when such contents are coagulated or cured tissue adhesive or sealant. Furthermore, it is believed that such taper should preferably be a gradual one. It has been observed that, where too drastic a taper is provided in the clearing pathway, initial proximal movement of the targeted coagulum creates a shunting pathway around the coagulum. This shunting pathway may significantly diminish the proportion of applied vacuum pressure onto the coagulum for withdrawal. However, some taper may be required for a particular fluid matrix to be cleared, due to the frictional dynamics of withdrawing the coagulum through the pathway. Thus, while a gradual taper such as that shown may be sufficient for many fluid delivery applications, other tapered geometries may be more preferable for a particular fluid application, as would be apparent to one of ordinary skill.

The operation of valve manifold (300) is shown schematically in FIGS. 13A–B in operating the suctioning invention to apply selected, varied levels of suction to suction conduit (260). In particular, the relationship between clearing aperture (for venting purposes) and suction aperture are shown in achieving different selected levels of applied suction at suction conduit (260).

FIG. 13A shows the valve manifold in the resting or venting position, similar to that shown in FIG. 12A. There is no suction at suction port (304), nor at clearing port (305) because neither of the respective suction or clearing apertures (314,316) is aligned therewith, and instead the wall of valve stem (310) blocks communication through those ports. Venting is achieved in this position either through vent aperture (318) or through clearing aperture (316), which communicates with atmospheric pressure above the top of valve housing (301) through vent port (302), or through both (bolded arrows). In one mode during initial actuation of valve manifold (300) to various actuated positions, vent aperture (318) is manually blocked and full venting is achieved through clearing aperture (316).

FIG. 13B shows the valve manifold after actuation to a suctioning position within the valve housing which is somewhere between the resting or venting position (such as in FIGS. 12A or 13A) and the first suction position (such as in FIG. 12B). It is to be understood by one of ordinary skill that, between these two positions, suction aperture (314) and clearing aperture (316) translate across and register at least in part with suction port (304) and vent port (302), respectively. It is to be further understood that, during this downward motion of valve stem (310), suction aperture (314) has an increasing cross-sectional area which registers with suction port (304), going from its short axis to its wide axis. Simultaneously, clearing aperture (316) instead has a decreasing cross-sectional area which communicates with atmospheric venting through vent port (302) as its wide axis leads its short axis downwardly into valve housing (301).

Further to the suction valving mechanism as shown in operation in FIGS. 13A–B, a combination of "venturi"-type and "trumpet"-type valve mechanisms are used to achieve controlled suction at suction conduit (260). The term "venturi"-type valve is herein intended to mean a valve mechanism that adjusts applied suction at a working pathway where applied suction is intended by adjusting the degree of parallel venting through at least one vent pathway. The term "trumpet"-type valve is herein intended to mean a valve mechanism which adjusts the applied suction at the working pathway by selectively occluding or opening the cross section of the conduit directly in the working pathway. Clearing aperture (316), when translated across the open vent port (302) and downwardly into valve housing (301), functions as an adjustable venturi-type valve to shunt applied vacuum in a selected manner away from another open suction pathway through suction conduit (260). Suction aperture (314), when translated across suction port (304), functions as a trumpet-type valve to directly adjust the resistance to applied vacuum to suction conduit (260).

In this combination suction valving mechanism of the present invention, it has been beneficially observed that a controllable range of vacuum pressures may be achieved at suction conduit (260), and that a zero vacuum state can also be achieved at that conduit. It is believed that the venturi valve mechanism arises from operating clearing aperture (316) as a vent, and together with the simultaneous adjusting of that vent with the adjusting of a trumpet valve component through the suction aperture operation, provides a controllable range of applied pressures. It is further believed that the inverse orientation of short and wide cross-sectional areas of the venturi (clearing aperture) and trumpet (suction aperture) valving apertures, in relation to the direction of travel during the combination valving function, further enhances the ability to control the applied suction to selected levels. In addition, the trumpet valve component arising from the operation of suction aperture (314) makes the completely closed, zero vacuum condition possible.

It is further contemplated that, while the inversely oriented tear-drop or diminished ellipse shapes for the suction and clearing apertures are considered particularly useful in controlling selected levels of applied suction to a working suction conduit, the invention is not so limited to that particular arrangement of aperture shapes. Various shapes other than the "tear-dropped" shape described and shown for suction and clearing apertures (314,316) may be acceptable in various modes of operating the assembly. For example, circular apertures may be used, or one of the suction or clearing apertures may be circular and the other may be a different shaped, such as the tear-drop shape or diminished ellipse.

More specifically regarding the diminished elliptical shapes of the particular embodiments, the ratio of the elongate axis length to the change in cross-sectional area between short and wide axes along that elongate axis may be adapted for a particular intended use. For example, it is believed that a longer elongate axis, with a more gradual change in cross-sectional area from the short axis to the wide axis of the shape, may provide for a longer length of actuating travel between selected levels of suction, and therefore may result in more sensitive control of minute changes in suction level.

Further to the shuttling operation of adjusting applied suction from selected conduits, FIGS. 13A–B also show the distal portions of shuttle valve (350) as it interacts and couples with the dispensing and suction assemblies. Each of the branched conduits (82,84) and also clearing conduit (270) are shown to include a slotted region, such as slotted region (83) in branched conduit (82) or slotted region (271) in clearing pathway (270), through which the respectively engaged valve portion may be slideably received. Dispensing valve portion (360) and clearing valve portion (370) are engaged within the slotted regions of dispensing conduit (70) and clearing conduit (270), respectively. Actuation of the shuttle valve components through these slotted regions for the purpose of selecting operable fluid pathways in a clearing function is further discussed with reference to FIGS. 14A–B below.

In actuating valve manifold (300) from the vent position to the first suction position (or somewhere therebetween as shown in FIGS. 13A–B), shuttle valve (350) remains in a resting reward position within the applicator portion. This is because, over the range of motion between the two respective valve manifold positions, the cam actuating surface on the valve actuator has not yet contacted the cam surface of shuttle valve (350) to actuate motion thereto (not shown). Further to this rearward resting position shown for shuttle valve (350), actuator dispensing apertures such as actuating dispensing aperture (364) on vertical spline (362) are aligned and registered with the interior lumens of each of branched conduits in their respective slotted regions, which alignment allows for fluid dispensing. However, actuator clearing aperture (374) on clearing valve portion (370) is out of alignment with the interior lumen of clearing conduit (270) in the slotted region thereof, and instead closed portion (376) of valve clearing portion (370) is aligned in that slotted region to block flow therethrough. Further detail as to the mechanism of actuating the valving mechanisms of shuttle valve (350) are further developed with respect to FIGS. 14A–B.

FIGS. 14A–B show schematic views of the role of valve manifold (300) and shuttle valve (350) in the clearing function of the suction assembly of the current invention. FIG. 14A shows the valve manifold positioning and applicator portion during the operation of dispensing a mixed fluid, while FIG. 14B shows a subsequent operation of clearing the mixed fluid from the applicator tip region.

FIG. 14A provides a schematic view of the valving operation of the device during use it tissue preparation prior to dispensing, as shown in perspective view in FIG. 1. Each of two different fluids is shown being dispensed through either branched channel (82) or branched channel (84). Shuttle valve (350) is in the reward resting position to allow the fluids to flow through the dispensing valve portions and mix in mixed conduit (92). The mixture is further shown being dispensed out tip dispensing aperture (14). Simultaneously the fluid delivery just described, valve manifold (300) is shown adjusted to the first suction position (or something close thereto) to allow for suction pathway (6) to couple vacuum pressure to the tip suction aperture (12).

FIG. 14B shows the same schematic view of FIG. 14A after fluid dispensing and during a clearing operation. Shuttle valve (350) is actuated into a forward actuated position. In this position fluid communication is blocked between vacuum conduit (250) and branched conduits (82, 84) via the closed portion (366) of dispensing valve portion (360). Also in this position, communication is opened between vacuum conduit (250) and mixed conduit (92), through clearing conduit (270), via clearing valve aperture (374). The seal members (FIGS. 11A–D) on the dispensing valve and clearing valve portions (360,370) allow for slidable engagement within the respective slotted portions of the engaging conduit lumens, yet substantially maintain fluid integrity at those slotted portions and around the engaging valve portions.

Thus, clearing pathway (7) is created in this shuttling operation, and the mixed fluid in mixed conduit (92) is shown in FIG. 14B as it is withdrawn due to suction through clearing pathway (270). Furthermore, by blocking communication between the branched portion (80) of dispensing conduit (70) and the mixed conduit (92) of dispensing conduit, contents proximal to the shuttle valve within the fluid dispensing pathway, including that in the supply reservoirs (not shown), are isolated from vacuum pressure and also from the contaminating coagulum being withdrawn from mixed conduit (92) (in the case of tissue adhesive applications).

It is further contemplated that the shuttle valve of the present invention may take a different form than that specifically described with reference to FIGS. 11A–D and 13A–14B without departing from the scope of the present invention. For example, rather than the shuttle valve shown and described, the slidable shuttling mechanisms of dispensing valve portion (360) and clearing valve portion (370) through slots in the engaging conduit lumens may be replaced with other types of individual valve mechanisms which may operate separately or in coordination. One example of a suitable alternative may be individual trumpet valve-type mechanisms engaged with each respective conduit lumen to selectively restrict flow therethrough. Any suitable mechanism which is apparent to one of ordinary skill from this disclosure and which allows for the desired selection of open and closed lumens in the dispensing and clearing conduits during the dispensing and clearing operations described is considered within the scope of the current invention. Therefore, where "shuttle valve" is used throughout this disclosure, it should be apparent that these other suitable valving alternatives are also contemplated.

It is to be further understood with reference to FIGS. 12A–14B that the ability to open vent aperture (318) to atmospheric pressure at any time by removing the actuating user's finger therefrom contributes a safety feature to the overall design. It is contemplated that, during some uses, the suction in the tip of the device may aggressively engage and hold tissue proximate to that tip. In a case where the valving mechanisms provided with the device may stick in an actuated position, or when very rapid release of suction is desired, opening vent aperture (318) immediately shunts most all of the applied suction out that port to thereby allow for rapid release of engaged tissue at the applicator tip.

Figure 15:
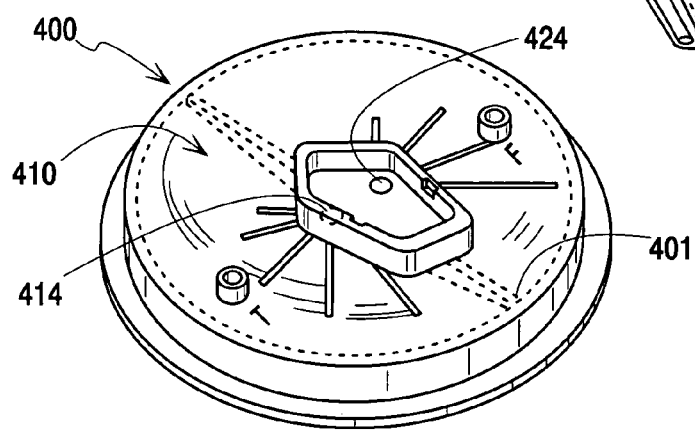
FIG. 15 is a perspective view of one preferred filling dispenser assembly used to fill the dispensing assembly of the supply device portion of the medical fluid applicator of FIG. 1.
Figure 16:
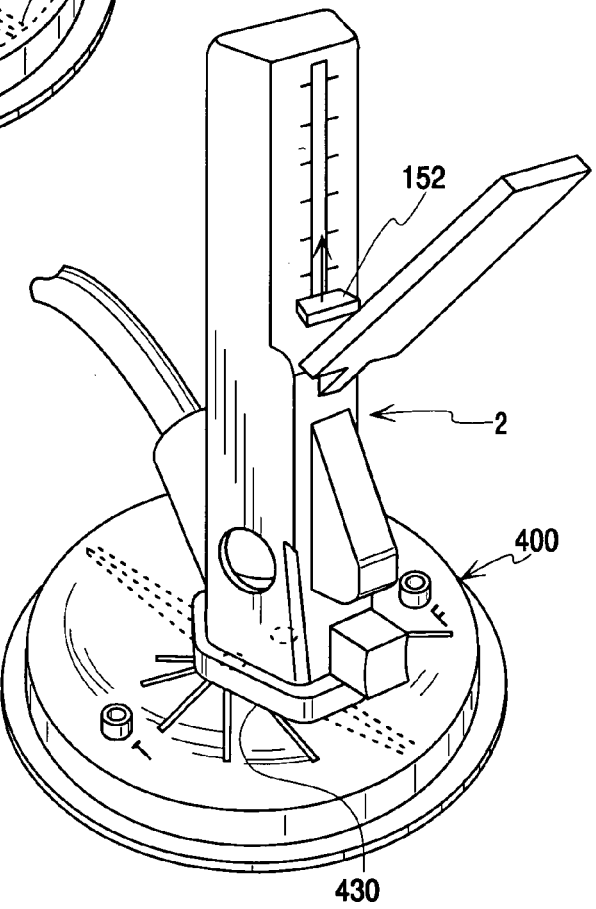
FIG. 16 is a perspective view of the dispenser assembly of FIG. 15 with the supply device portion of the medical fluid applicator of FIG. 1 engaged thereto in a predetermined filling orientation.

In another variation of the current suctioning device invention, supply device portion (2) of the overall combination medical fluid applicator assembly is shown in FIGS. 15 and 16 during a filling operation using a beneficial design of filling dispenser. Further detail of the beneficial filling dispenser is shown for filling dispenser (400) in FIGS. 17A–E.

As shown generally in FIGS. 15 and 16, filling dispenser (400) includes first and second filling reservoirs (410,420) that are separated and isolated by a divider (401). Filling reservoirs (410,420) include dispenser filling ports (414, 424), respectively, which are adapted for use in filling the filling reservoirs with the desired fluids to be transferred to the supply device portion of the medical fluid applicator for delivery. In one variation, the filling reservoirs may be provided "pre-loaded" with liquid components, or in some cases dried components, of the desired fluid, in which case dispenser filling ports (412,422) may be used for additives such as catalysts, buffers, or other agents. Filling reservoirs (410,420) further include applicator filling ports (414,424), respectively, which are adapted to couple to supply ports of the supply device via keyed coupling (430).

As shown in overview in FIG. 16, keyed coupling (430) is adapted to engage supply device portion (2) such that the fluid reservoirs of the supply device portion are coupled to the applicator filling ports, and thus the filling reservoirs, in a predetermined orientation. In other words, only one, predetermined fluid reservoir of the supply device portion may be coupled to each filling reservoir of the filling dispenser. In the embodiment shown in FIG. 16, the actuating assembly is operated in a reverse mode for filling the fluid reservoirs. Tab (152) of the visual volume indicator is also adapted as a filling actuator, which may be manually withdrawn in the proximal direction to provide suction into the fluid reservoirs of the device and thus fill them with fluids from the coupled filling reservoirs.

Figure 17A:
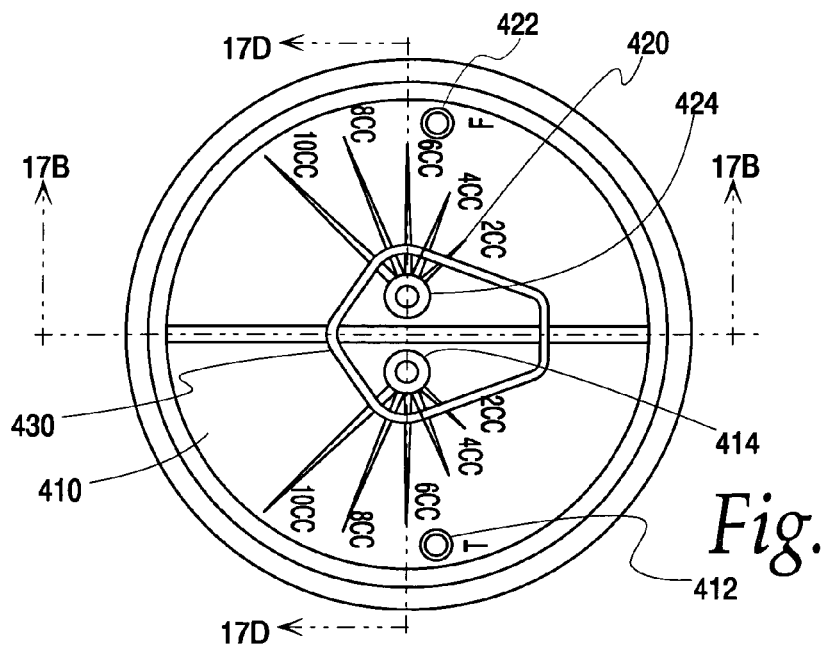
FIG. 17A is a top plan view of the filling dispenser assembly shown in FIG. 15.
Figure 17B:
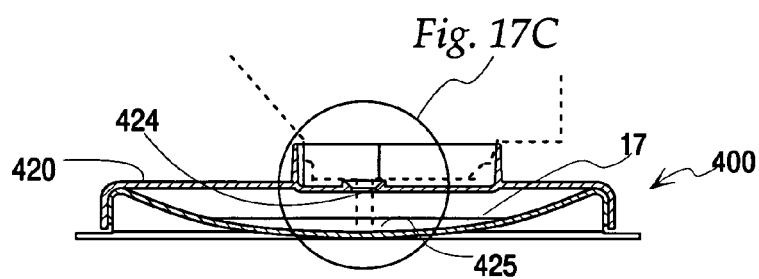
FIG. 17B is a sectional elevational view taken along line 17B—17B of FIG. 17A.
Figure 17C:
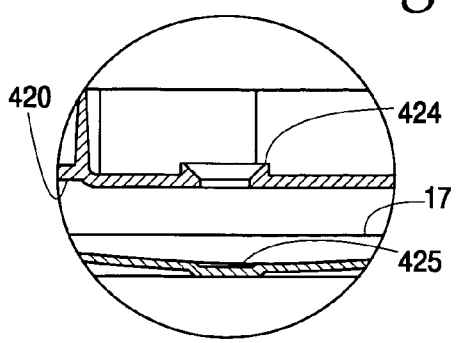
FIG. 17C is an exploded sectional elevational view of one supply device coupling region shown in FIG. 17B.
Figure 17E:
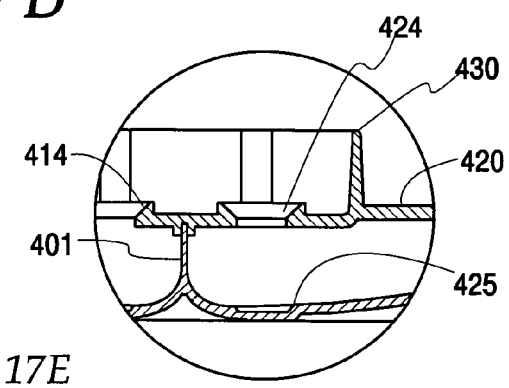
FIG. 17E is an exploded sectional elevation view similar to FIG. 17C, except showing the region indicated in FIG. 17D.
Figure 17D:
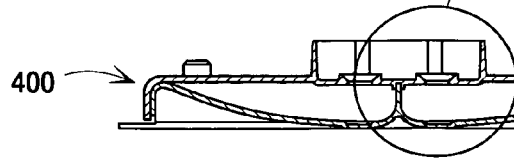
FIG. 17D is a similar sectional elevational view to FIG. 17B, except taken along line 17D—17D of FIG. 17A.

FIG. 17B depicts one of the filling reservoirs (420) which is filled at least partially with fluid (17), which may for example be one part of a two-part fluid, such as one of two parts which mix to form fluid (16) shown dispensed from medical fluid applicator (1) in FIG. 1. The portion of the supply device which couples with the applicator filling ports, which may be the supply ports respectively coupled to the fluid reservoirs as shown in FIG. 3, is shown in shadowed view in FIG. 17B. Here one supply port of the medical fluid applicator is shown coupled to applicator filling port (424) and is positioned within well (425) at the bottom of the respective filling reservoir (420). In this design, the efficiency in withdrawing a substantial portion of the fluid in the filling reservoirs is enhanced. FIGS. 17C–E show various views to enhance the understanding of the various features of filling dispenser (400) just described.

In the keyed coupling shown and described, the dispensing characteristics for each fluid reservoir may be specially adapted for the specific type of fluid which is contained in the predetermined filling reservoir to which it will couple. For example, each part of a two-part fluid may be contained in each filling reservoir. The two parts may be intended to mix in a particular ratio, such as in a ratio of one part of one fluid to two parts of the other. In this case, the fluid reservoirs of the supply device may have differing bore cross-sections such that one full actuation stroke constitutes one volumetric unit of fluid delivery from one fluid reservoir, and two volumetric unit of fluid delivery in the other. By keying the coupling between the supply device and the filling dispenser as provided in this variation, the proper fluid may always be filled into each fluid reservoir.

It is to be understood by one of ordinary skill that the present invention is not to be limited to specific types of fluids to be filled in the medical fluid applicator, and particularly in regards to the filling operation provided with the filling dispenser just described. For example, biologic and synthetic tissue adhesives, wound closure sealants, and various pharmacologic agents may be dispensed from the filling dispenser and subsequently applied in medical procedures with the medical fluid applicator of the present invention.

It is, however, believed that the various beneficial dispensing, suctioning, and clearing functions of the present invention present particularly useful benefits in the medical application of delivering of biologic or other adhesives to tissue surfaces. In this regard, "adhesive" is herein used throughout this disclosure to collectively describe substrates which are either useful literally as adhesives for adhering biological tissues, and/or which are useful as sealants or closure substrates used to seal spaces within the body, such as for wound closure procedures.

More particularly, it is further believed that delivery tissue adhesives or sealants which cure or coagulate relatively rapidly may present a particular need for the clearing feature provided with the current invention and described in detail above. The term "cure" and derivatives thereof is herein used throughout this disclosure to mean any mechanism giving rise to substantive physical change in the substrate which affects its mechanical and fluid flow properties, such as for example "coagulating", "congealing," or "cross-linking" mechanisms. Furthermore, such "quick" curing substrates often come in two-part form which, upon mixing, activates a rapid curing response.

Examples of such tissue adhesives or sealants the delivery of which may be enhanced by use of the clearing function just described are many. For example, several composite tissue adhesives ("CTA") have been described which may require retrograde clearing intermittently during a fluid delivery procedure. One example of a suitable CTA for use with the present delivery invention may be fibrin-based composites such as fibrin-collagen composites. Furthermore, polyethylene glycol (PEG) cross-linked composites, such as PEG-collagen or PEG-hyaluronic acid composites may be suitable. A further example of a two-part tissue adhesive is disclosed in EP 592 242 to Edwardson et al, wherein a fibrin monomer is coadministered with a buffer solution in a tissue sealant operation.

Other examples of suitable substrates for delivery with the current invention include certain classes of protein polymers which have biologic adhesive qualities, such as an amplified fibrinogen-like protein which is activated either by chemical cross-linking, such as with glutaraldehyde, or by enzymatic cross-linking such as with thrombin or Factor XIIA. Furthermore, plain plasma mixtures, as well as platelet concentrates, have been disclosed for tissue adhering procedures, and may rapidly form coagulums in delivery conduits during delivery procedures. Synthetic polymers such as cyanoacrylate adhesives or the like may also be used for tissue adhering or sealing procedures and which may cure in the delivery conduit such that suction withdrawal may be beneficial.

Still further, other fluids in addition to or in the alternative to tissue adhesives or sealants may have curing properties during delivery which would benefit by the clearing mode of operating the present inventive delivery device. For example, drug delivery fluids such as synthetic polymer substrates (PEG), bioerodable polymers, non-erodable polymeric excipients, hydrogels, cultured cells, or various other forms of pharmaceuticals (such as growth factor) or biologics may be delivered as a substrate which clogs a dispensing conduit during medical fluid delivery procedures.

In addition to the broad field of substrates which may be suitable for use with the present invention, the present invention is also not limited to only the particular structural embodiments which are described in detail above. For example, FIGS. 18A–C show a further variation of both the supply device portion and the applicator portion of the medical fluid applicator invention. Furthermore, FIGS. 19–20C show another alternative variation for the applicator portion of the medical fluid applicator.

The medical fluid applicator (500) shown in overview in FIGS. 18A–C includes all of the internal componentry shown and described for the medical fluid applicator variations above, with some modifications to the dispensing and suction actuating assemblies in the supply device portion, and also to the applicator tip configuration of the applicator portion.

FIGS. 18A–B show applicator portion (503) of medical fluid applicator (500) to include an alternative variation for applicator tip (510) to that shown for the previous embodiments. Due to the elongated dimensions for applicator tip (510), it is believed that this variation has particularly beneficial application in moderately invasive surgical procedures for tissue adhesion or wound sealing, such as in less-invasive bypass procedures that are previously known and described in the art. It is to be appreciated by reference to FIGS. 18A–B in view of the previously shown and described embodiments that the internal structures of applicator portion (503) (not shown) are similar to that described for applicator portion (3) of those previous embodiments.

For example, applicator portion (503) includes a dispensing conduit that has a branched portion and a mixed portion, a suction conduit, a clearing conduit, and a shuttle valve such as those components previously described. However, in this variation, the branched portion of the dispensing conduit, the suction conduit, and the clearing conduit are all provided in an elongated form through the extended length of applicator tip (510). The mixed conduit component of the dispensing conduit, and also the distal portion of the shuttle valve which includes the dispensing and clearing valve portions, are preferably located in the distal region (512) of applicator tip (510). It is to be further understood that the suction conduit and the mixed portion of the dispensing conduit terminate distally in tip suction aperture (512) and tip dispensing aperture (524), respectively, as shown in FIG. 18A.

The actuating assembly for medical fluid applicator (500) is further shown in FIG. 18A, and includes a handle (505) which has an actuating trigger (520) coupled therewith. This variation is adapted for single handed use in actuating fluid dispensing. By gripping handle (505) and actuating trigger (520) in a user's hand, compressing the trigger against the handle actuates the dispensing assembly within the device to dispense fluids a predetermined incremental amount. Actuating trigger (520) includes a spring-bias and a full "stroke" range of motion which may be similar to the spring-bias and "stroke" described for the previous embodiments, such as with reference to FIG. 5. Furthermore, the coupling of actuating trigger (520) to the other components of the actuating assembly (not shown) may be similar to that described for the previous variation of FIG. 5, including the rack and pawl mechanism, and further including the audible and visual volume indicators previously described, as would be apparent to one of ordinary skill.

Also shown in FIG. 18A is a valve actuator (530) which is also coupled to handle (505) and is also adapted for single-handed use in a similar manner as actuating trigger (520). By depressing valve actuator (520) to various actuated positions relative to handle (505), a valve manifold (not shown) within the interior of the supply device portion (502) is adjusted to various positions to create a venting pathway, a suction pathway, or a clearing pathway. Furthermore, actuated motion of valve actuator (520) also selectively positions the shuttle valve component of the device (not shown) in order to close suction to the suction conduit and open communication for suction to the mixed portion of the dispensing conduit via the clearing conduit. The mechanisms provided by the valve manifold and the shuttle valve in this variation are the same as those shown and described for the previous embodiments, but for the coupling of valve actuator (520) to the manifold and the shuttle valve, which would be apparent to one of ordinary skill by this disclosure.

A further variation of the medical fluid applicator of the present invention is provided by reference to medical fluid applicator (600) in FIGS. 19A–20C. This variation includes all of the mechanical dispensing features, valving features, and actuating features of the previous embodiments, but includes only a single dispensing conduit (660) at the applicator tip (610) and omits the suction conduit feature of the previous embodiments. By this alternative variation, it is to be understood that the utility of applied suction for tissue preparation may be done in series with fluid dispensing through the same conduit, and need not be contemporaneous to fluid delivery through two, adjacent conduits as provided in the previous embodiments.

In this single conduit variation of the invention, it is contemplated that the device may be used during one particularly prolonged period for suction and in another prolonged period for dispensing. For this reason, it is less convenient to have a constant spring-bias to a rearward position for the shuttle valve, such that the valve must be manually actuated against the resting spring bias in order to close the dispensing pathway and open the suction/clearing pathway through the common conduit. Therefore, it is preferred in this variation to provide a detent locking mechanism (not shown) so that the shuttle valve may be temporarily locked into one of two positions for dispensing or clearing, respectively, such as the detent locking mechanism which is commonly used in opening and closing ball-point ink pens.

Figure 20A:
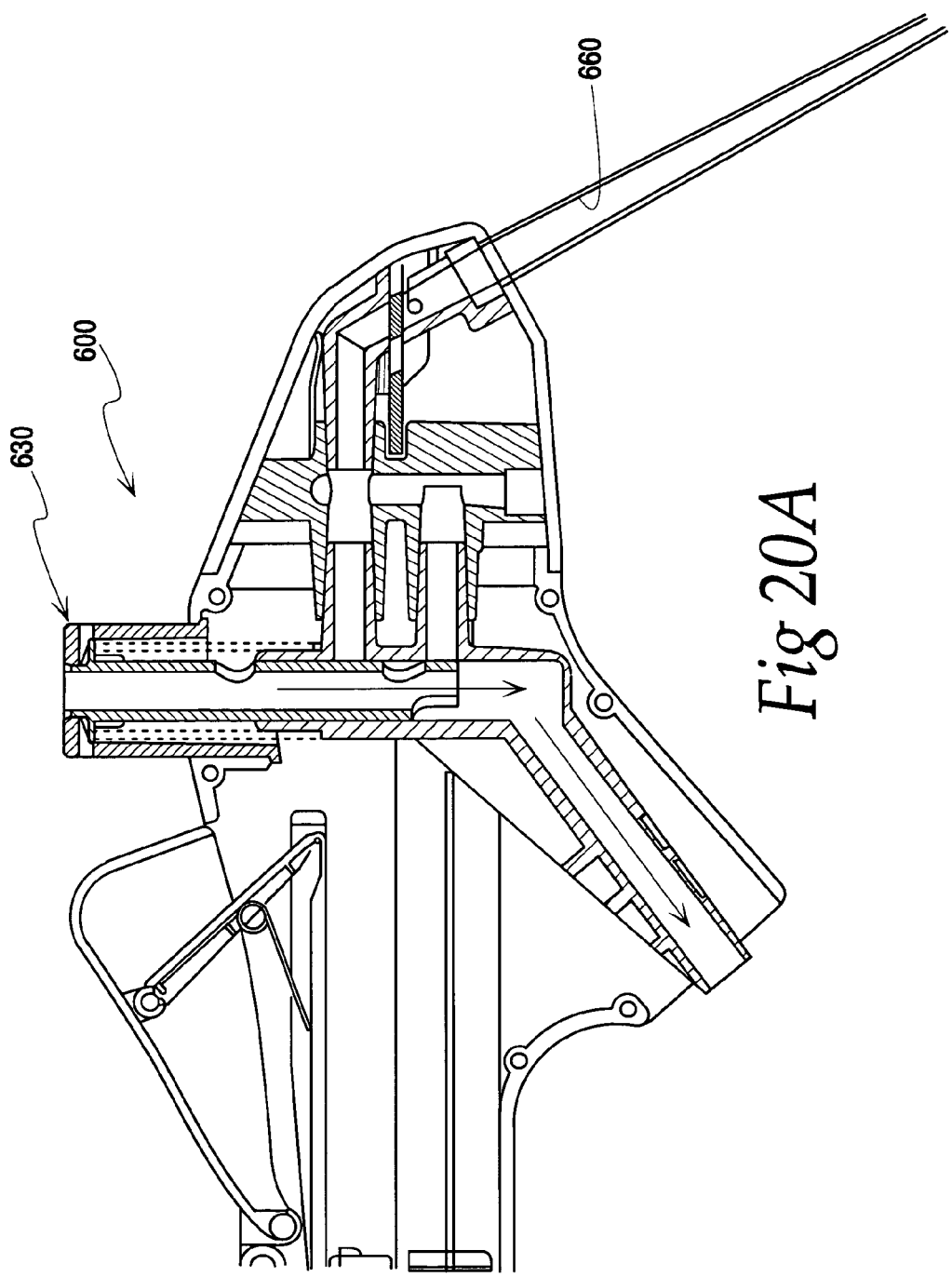
FIGS. 20A–C are exploded views of the applicator tip portion of the assembly shown in FIG. 19D, showing the valve manifold in sequential modes of operation in creating a vent pathway, a suction pathway, and a clearing pathway, respectively.
Figure 20B:
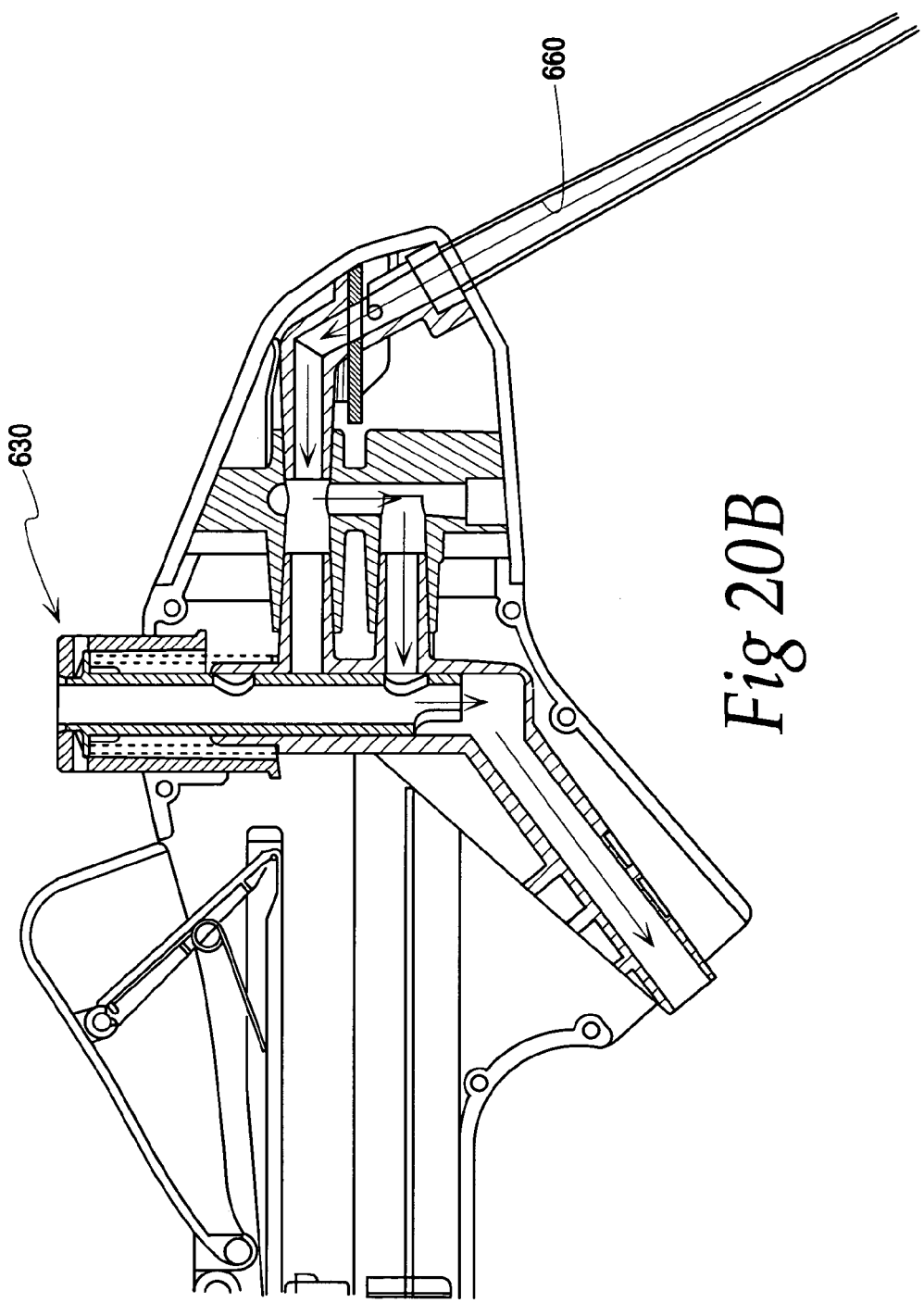
Figure 20C:
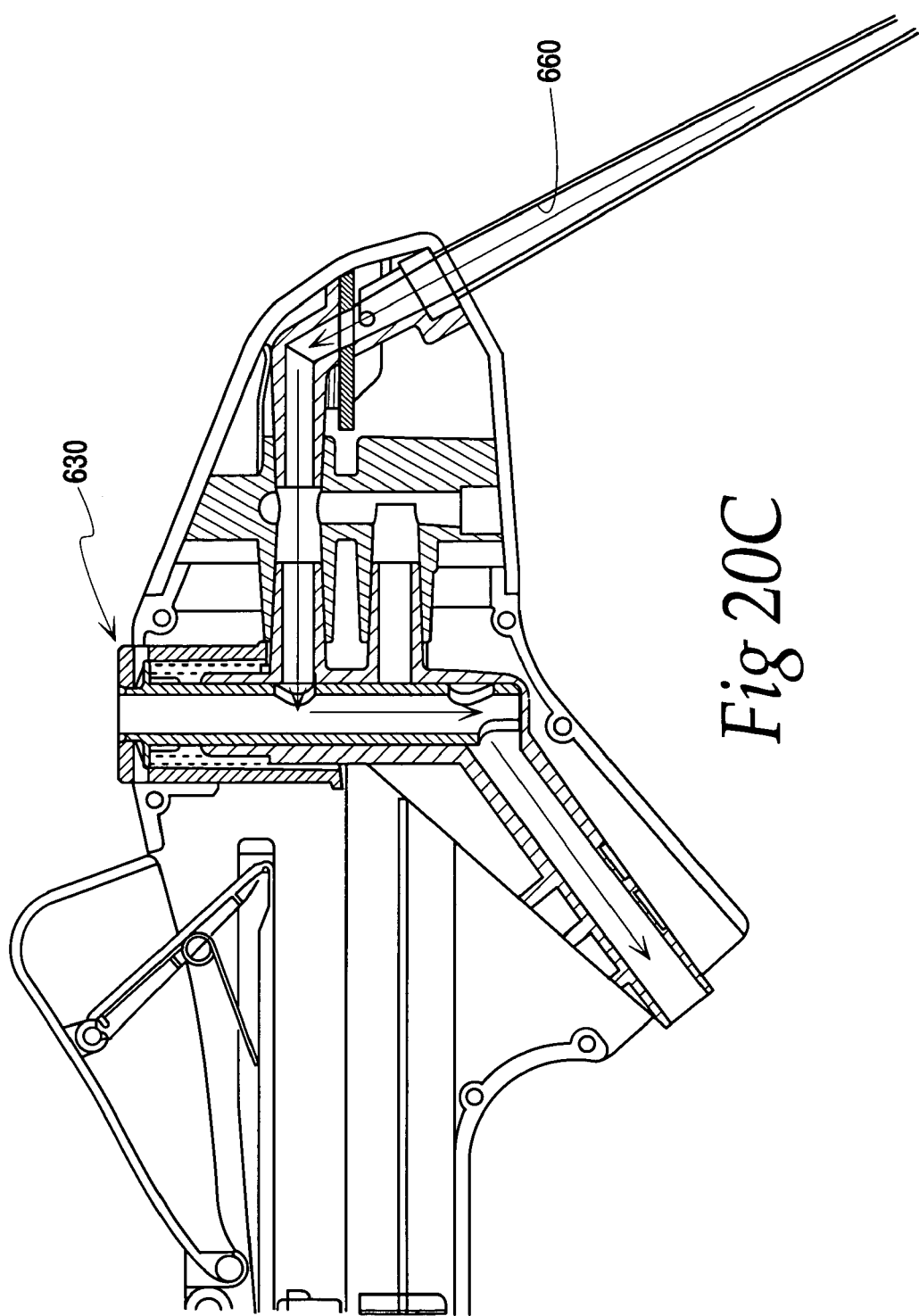

FIGS. 20A–C show various operating modes of this variation in a similar manner to FIGS. 12A–C in describing operation of the previous embodiment associated therewith. In FIG. 20A, valve manifold (630) is shown in a resting or venting position similar to that of FIG. 12A. In FIG. 20B, valve manifold (630) is shown actuated in a first suction position. In FIG. 20C, valve manifold (630) further shown in a second clearing position, wherein the distal mixed region of dispensing conduit (660) is retrogradedly cleared of its contents.

It should be understood by one of ordinary skill from the preceding disclosure that the present invention is broader than the particular embodiments described. Suitable alternatives to the particular described embodiments which are apparent to one of ordinary skill from this disclosure are considered to be included within the scope of the present invention.

What is claimed is:

1. A method of applying a fluid adhesive material and suction from a handheld applicator to a work surface:
   a) operating a manual actuator to dispense adhesive from one or more adhesive component reservoirs to the work surface;
   b) ceasing operation of the manual actuator whereby adhesive dispensing terminates;
   c) operating a control valve to admit a flow of suction along a suction pathway from a vacuum source and apply suction to the work surface; and
   d) operating the control valve to terminate the flow of suction to the work surface.

2. A method according to claim 1 further comprising operating the control valve to admit suction from a vacuum source and apply suction to prepare the work surface prior to first operating the manual actuator to dispense adhesive.

3. A method according to claim 1 further comprising operating the manual actuator to dispense adhesive from one or more adhesive component reservoirs to the work surface after operating the control valve to terminate the flow of suction to the work surface.

4. A method according to claim 3 further comprising again ceasing operation of the manual actuator and again operating the control valve to admit suction.

5. A method according to claim 1 wherein the handheld applicator comprises an adhesive aperture through which the adhesive is dispensed and a suction aperture through which the flow of suction is delivered and wherein the method further comprises aligning the adhesive aperture and the suction aperture to be equidistant from the work surface.

6. A method according to claim 1 further comprising setting the control valve to any one of a continuous range of settings between full suction and no suction.

7. A method according to claim 1 further comprising adjustably venting the suction pathway to atmosphere.

8. A method according to claim 7 wherein the venting is adjustable between full venting of suction with no application of suction to the work surface and no venting of suction with full suction applied to the work surface and includes intermediate conditions wherein suction is partially applied to the work surface and partially vented to atmosphere.

9. A method according to claim 7 further comprising adjusting the negative pressure applied by the vacuum source to the suction pathway.

10. A method according to claim 9 wherein the adjustments of negative pressure and the adjustments to venting are effected simultaneously to obtain a desired suction at the work surface.

11. A method of applying a fluid adhesive material and suction from a handheld applicator to a work surface:
    a) operating a control valve to admit a desired level of suction along a suction pathway from a vacuum source and apply the level of suction to a first unprepared portion of the work surface to create a first prepared portion;
    b) operating the valve to terminate the flow of suction to the work surface;
    c) operating a manual actuator to dispense adhesive from one or more adhesive component reservoirs to the first prepared portion of the work surface.

12. A method according to claim 11 further comprising setting the control valve to any one of a continuous range of settings between full suction and no suction.

13. A method according to claim 11 further comprising adjustably venting the suction pathway to atmosphere.

14. A method according to claim 13 wherein the venting is adjustable between full venting of suction with no application of suction to the work surface and no venting of suction with full suction applied to the work surface and includes intermediate conditions wherein suction is partially applied to the work surface and partially vented to atmosphere.

15. A method according to claim 13 further comprising adjusting the negative pressure applied by the vacuum source to the suction pathway.

16. A method according to claim 15 wherein the adjustments of negative pressure and the adjustments to venting are effected simultaneously to obtain a desired suction at the work surface.

* * * * *